United States Patent
Juncker et al.

(10) Patent No.: US 9,481,945 B2
(45) Date of Patent: Nov. 1, 2016

(54) METHODS AND DEVICES FOR MULTIPLEXED MICROARRAY MICROFLUIDIC ANALYSIS OF BIOMOLECULES

(75) Inventors: David Juncker, Verdun (CA); Huiyan Li, Montreal (CA)

(73) Assignee: THE ROYAL INSTITUTION FOR THE ADVANCEMENT OF LEARNING / MCGILL UNIVERSITY, Montreal, QC (CA)

( * ) Notice: Subject to any disclaimer, the term of this patent is extended or adjusted under 35 U.S.C. 154(b) by 29 days.

(21) Appl. No.: 13/597,362

(22) Filed: Aug. 29, 2012

(65) Prior Publication Data

US 2013/0053273 A1    Feb. 28, 2013

Related U.S. Application Data

(60) Provisional application No. 61/528,898, filed on Aug. 30, 2011, provisional application No. 61/528,792, filed on Aug. 30, 2011.

(51) Int. Cl.
*C40B 60/02*    (2006.01)
*G01N 33/543*   (2006.01)
(Continued)

(52) U.S. Cl.
CPC ......... *C40B 60/02* (2013.01); *G01N 33/54366* (2013.01); *B01J 2219/0074* (2013.01);
(Continued)

(58) Field of Classification Search
CPC .. B01L 3/50853; B01L 3/5088; B01L 3/563; B01L 2200/0642; B01L 2200/16; B01L 2300/0819; B01L 2300/0822; B01J 2219/00382; B01J 2219/00533; B01J 2219/00704; B01J 2219/00725; B01J 2219/0074; C04B 60/02; C04B 20/02
See application file for complete search history.

(56) References Cited

U.S. PATENT DOCUMENTS 4,647,524 A  *  3/1987  Sullivan ............... B23K 35/224
                                                   430/258
4,840,714 A  *  6/1989  Littlehales .................... 204/464
(Continued)

FOREIGN PATENT DOCUMENTS

WO    WO2008/157640 A2  * 12/2008
WO    WO 2009137521 A2  * 11/2009
WO    WO2010/111265 A1  *  9/2010

OTHER PUBLICATIONS

J.M.K. Ng et al., Components for Integrated Poly (dimethylsiloxane) Microfluidic Systems .Electrophoresis, vol. 23, pp. 3461-3473.
(Continued)

*Primary Examiner* — Jeremy C Flinders
(74) *Attorney, Agent, or Firm* — Norton Rose Fulbright Canada LLP

(57) ABSTRACT

Rapid and specific detection of biological cells and biomolecules is important to biological assays across diverse fields including genomics, proteomics, diagnoses, and pathological studies. Microarrays and microfluidics increasingly dominate such detection techniques due to the ability to perform significant numbers of tests with limited sample volumes. A snap chip assembly is provided for the transfer of a microarray of reagents within semi-spherical liquid droplets on a transfer chip to a target assay microarray on an assay chip following assembly of the two chips and physical contact of the droplets with the target array. Reagents in nanoliter quantities are spotted on both chips and selectively transferred as liquid droplets between transfer chip and assay chip within the contact areas. Using the snap chip structure the inventors performed immunoassays with colocalization of capture and detection antibodies with 10 targets and bead-in-gel droplet microarrays with 9 targets in the low pg/ml regime.

15 Claims, 25 Drawing Sheets

(51) Int. Cl.
  G01N 33/68    (2006.01)
  C40B 20/02    (2006.01)
  B01L 3/00     (2006.01)
(52) U.S. Cl.
  CPC .......... B01J2219/00382 (2013.01); B01J 2219/00533 (2013.01); B01J 2219/00704 (2013.01); B01J 2219/00725 (2013.01); B01L 3/5088 (2013.01); B01L 3/50853 (2013.01); B01L 3/563 (2013.01); B01L 2200/0642 (2013.01); B01L 2200/16 (2013.01); B01L 2300/0819 (2013.01); B01L 2300/0822 (2013.01); C40B 20/02 (2013.01); G01N 33/6845 (2013.01)

(56) References Cited

U.S. PATENT DOCUMENTS 7,235,307 B2    6/2007   Chen et al.
2011/0294703 A1*  12/2011  Jeon et al. .......... 506/23

OTHER PUBLICATIONS

L. Gervais et al.,Toward One-Step Point-of-Care Immunodiagnostics using Capillary-Driven Microfluidics and PDMS Substrates, Lab on a Chip, vol. 9, pp. 3330-3337.
R.A. George et al., Ceramic Capillaries for use in Microarray Fabrication, Genome Res., vol. 11, pp. 1780-1783.
R. Safavieh et al., Straight SU-8 Pins, J. Micromechanics and Microengineering, vol. 20, 055001, 2010.
H. Li et al., Hydrogel Droplet Microarrays with Trapped Antibody-Functionalized Beads for Multiplexed Protein Analysis 4, Lab on a Chip, vol. 11, pp. 528-534.
M. Pia-Roca et al., Addressable Nanowell Arrays Formed Using Reversibly Sealable Hybrid Elastomer-Metal Stencils, Anal. Chem., vol. 82, pp. 3848-3855.
C. Steinert et al., TopSpotTM Vario: A Novel Microarrayer System for Highly Flexible and Highly Parallel Picoliter Dispensing, Biomed. Microdevices, vol. 11, 755-761.
W. Du et al., SlipChip, Lab on a Chip, vol. 9, 2286-2292.
Du and W. Liu et al., SlipChip for Immunoassays in Nanolitre Volumes, Anal. Chem., vol. 82, pp. 3276-3282.
M.Y. Lee et al., Metabolizing Enzyme Toxicology Assay Chip, MetaChip for High-Throughput Microscale Toxicity Analyses, Proc. Natl. Acad. Sci. U. S. A., vol. 102, pp. 983-987.
T.G. Fernandes et al., Three-Dimensional Cell Culture Microarray for High-Throughput Studies of Stem Cell Fate, Biotechnol and Bioeng., vol. 106, pp. 106-118.
M-Y. Lee et al., 5 Three-dimensional Cellular Microarray for High-Throughput Toxicology Assays, Proc. Natl. Acad. Sci. U. S. A, vol. 105, pp. 59-63.
Wu et al., A Sandwiched Microarray Platform for Benchtop Cell-Based High Throughput Screening, Biomaterials, vol. 32, pp. 841-848.
Kwong et al., Drug-Eluting Microarrays for Cell-Based Screening of Chemical-Induced Apoptosis, Anal. Chem., vol. 33, pp. 4118-4125.
Bilang-Bleuel et al., Intrastriatal injection of an adenoviral vector expressing glial-cell-line-derived neurotrophic factor prevents dopaminergic neuron degeneration and behavioral impairment in a rat model of Parkinson disease, Proc. Natl. Acad. Sci. USA, vol. 94, pp. 8818-8823, Aug. 1997, Neurobiology.
Murari et al.—Wireless Multichannel Integrated Potentiostat for Distributed Neurotransmitter Sensing, Proceedings of the 2005 IEEE Engineering in Medicine and Biology 27th Annual Conference Shanghai, China, Sep. 1-4, 2005, pp. 7329-7332.
M. Kuwata et al., Sliding Micro Valve Injection Device for Quantitative Nano Liter Volume, 8 the Int. Conf. Miniatunzed Systems for Chemistry and Life Sciences, 2004, pp. 342-344.

R. Briard et al., Crack Bridging Mechanism for Glass Strengthening by Organosilane Water-based Coatings, J. Non-Cryst. Solids, vol. 351, pp. 323-330.
Mandel et al., Midbrain injection of recombinant adeno-associated virus encoding rat glial cell line-derived neurotrophic factor protects nigral neurons in a progressive 6-hydroxydopamine-induced degeneration model of Parkinson's disease in rats, Proc. Natl. Acad. Sci. USA, vol. 94, pp. 14083-14088, Dec. 1997, Neurobiology, pp. 14083-14087.
Akerud et al., Neuroprotection through Delivery of Glial Cell Line-Derived Neurotrophic Factor by Neural Stem Cells in a Mouse Model Parkinson's Disease, The Journal of Neuroscience, Oct. 15, 2001, 21(20) pp. 8108-8118.
J.W. Findlay et al., Appropriate Calibration Curve Fitting in Ligand Binding Assays, AAPS Journal, vol. 9, pp. E260-267.
Kearns et al., GDNF Protection against 6-OHDA: Time Dependence and Requirement for Protein Synthesis, The Journal of Neuroscience, Sep. 15, 1997, 17(18) pp. 7111-7118.
C. Pfleger et al., Effect of serum content and diluent selection on assay sensitivity and signal intensity in multiplex bead-based immunoassays, vol. 329, pp. 214-218.
Rutkowski et al., Cytokine Serum Levels in Soft Tissue Sarcoma Patients: Correlations with Clinico-Pathological Features and Prognosis, Int. J. Cancer, vol. 100, pp. 463-471.
S. Fiorilli et al. Vapor-Phase Self-Assembled Monolayers of Aminosilane on Plasma-Activated Sillicon Substrates, J. Colloid and Interface Science, vol. 321, pp. 235-241.
F. Zhang et al., Chemical Vapor Deposition of Three Aminosilanes on Si licon Dioxide: Surface Characterization, Stability, Effects of Silane Concentration, and Cyanine Dye Adsorption, Langmuir, vol. 26(18), pp. 14648-14654.
Rascol et al., A Five-Year Study Of The Incidence Of Dyskinesia In Patients With Early Parkinson's Disease Who Were Treated With Ropinirole Or Levodopa, The New England Journal of Medicine, May 18, 2000, pp. 1484-1491.
Kong et al., Serum HER-2 concentration in patients with primary breast cancer, pp. 373-376, http://jcp.bmj.com/ on May 27, 2016—Published by group.bmj.com.
Takahashi et al, Association of Serum Endoglin with Metastasis in Patients with Colorectal, Breast, and Other Solid Tumors, and Suppressive Effect of Chemotherapy on the Serum Endoglin, Clinical Cancer Research, vol. 7, 524-532, Mar. 2001.
Aliustaoglu et al., Preoperative serum leptin levels in patients with breast cancer, Med. Oncol. (2010) 27 pp. 388-391.
Bramwell et al, Serial Plasma Osteopontin Levels Have Prognostic Value in Metastatic Breast Cancer, Clin Cancer Res, 2006;12(11) Jun. 1, 2006, pp. 3337-3343.
Poustinchi et al. Low Power Noise Immune Circuit for Implantable CMOS Neurochemical Sensor Applied in Neural Prosthetics, Proceedings of the 5th International IEEE EMBS Conference on Neural Engineering Cancun, Mexico, Apr. 27-May 1, 2011, pp. 695-699.
Scholl et al, Circulating levels of the macrophage colony stimulating factor CSF-1 in primary and metastatic breast lancer patients. A pilot study., Breast Cancer Research and Treatment 39: 275-283, 1996. Kluwer Academic Publishers. Printed in the Netherlands.
Kim et al, The multiplex bead array approach to identifying serum biomarkers associated with breast cancer, http://breast-cancer-research.com/content/11/2/R22.
Yurkovetsky et al, Multiplex Analysis of Serum Cytokines inMelanoma Patients Treated with Interferon-A2b, Clin Cancer Res 2007;13(8) Apr. 15, 2007, pp. 2422-2428.
ENZ—Circuit Techniques for Reducing the Effects of Op-Amp Imperfections: Autozeroing, Correlated Double Sampling, and Chopper Stabilization, Proceedings of the IEEE, vol. 84, No. 11, Nov. 1996, pp. 1584-1614.
Pla-Roca et al., Antibody Colocalization Microarray: A Scalable Technology for Multiplex Protein Analysis in Complex Samples, Molecular & Cellular Proteomics, vol. 11, pp. 1-12.
Y. Cai et al., Channel-Free Shear Driven Circular Liquid Chromatography, Lab on a Chip, vol. 8, pp. 1784-1786. The "SlipChip".
G. Desmet et al.. The Possibility of Generating High-Speed Shear-Driven Flows and Their Potential Application in Liquid Chromatography, Anal. Chem., vol. 72, pp. 2160-2165.

(56) References Cited

OTHER PUBLICATIONS

Dose Response to Intraventricular Glial Cell Line-Derived Neurotrophic Factor Administration in Parkinsonian Monkeys1 Zhiming Zhang, 2 Yasuyuki Miyoshi, 2 Paul A. Lapchak, 4 Frank Collins, 4 Dana Hilt, 5 Carl Lebel, 6 Richard Kryscio3 and Don M. Gash2 Anatomy and Neurobiology, University of Kentucky Medical center, Lexington, Kentucky Accepted for publication May 2, 1997.

Robinson et al., Detecting Subsecond Dopamine Release with Fast-Scan Cyclic Voltammetry in Vivo, Clinical Chemistry 49:10, pp. 1763-1773 (2003).

* cited by examiner

Section X-X $d_{POST}$ $d_{RECESS}$

Section Y-Y

1700A

1700B

METHODS AND DEVICES FOR MULTIPLEXED MICROARRAY MICROFLUIDIC ANALYSIS OF BIOMOLECULES

CROSS-REFERENCE TO RELATED APPLICATIONS

This patent application claims the benefit of U.S. Provisional Patent Application 61/528,898 filed Aug. 30, 2011 entitled "Methods and Devices for Multiplexed Microarray Microfluidic Analysis of Biomolecules" and U.S. Provisional Patent Application U.S. 61/528,792 filed Aug. 30, 2011 entitled "Methods and Devices for Multiplexed Microarray Microfluidic Analysis of Biomolecules."

FIELD OF THE INVENTION

This invention relates to the field of bio-analysis and more particularly to a method of providing multiplexed microfluidic analysis via microarray-to-microarray transfer.

BACKGROUND OF THE INVENTION

Rapid and specific detection of biological cells and biomolecules, such as red blood cells, white blood cells, platelets, proteins, DNA, and RNA, has become more and more important to biological assays that form a crucial element in diverse fields such as genomics, proteomics, diagnoses, and pathological studies. For example, the rapid and accurate detection of specific antigens and viruses is critical for combating pandemic diseases such as AIDS, flu, and other infectious diseases. Also, due to faster and more specific methods of separating and detecting cells and biomolecules, the molecular-level origins of diseases are being elucidated at a rapid pace, potentially ushering in a new era of personalized medicine in which a specific course of therapy is developed for each patient. To fully exploit this expanding knowledge of disease phenotype, new methods for detecting multiple biomolecules (e.g. viruses, DNA and proteins) simultaneously are required. Such multiplex biomolecule detection methods must be rapid, sensitive, highly parallel, and ideally capable of diagnosing cellular phenotype.

One specific type of biological assay increasingly used for medical diagnostics, as well as in food and environmental analysis, is the immunoassay. An immunoassay is a biochemical test that measures the level of a substance in a biological liquid, such as serum or urine, using the reaction of an antibody and its antigen. The assay takes advantage of the specific binding of an antibody to its antigen. Monoclonal antibodies are often used as they only usually bind to one site of a particular molecule, and therefore provide a more specific and accurate test, which is less easily confused by the presence of other molecules. The antibodies picked must have a high affinity for the antigen (if there is antigen in the sample, a very high proportion of it must bind to the antibody so that even when only a few antigens are present, they can be detected). In an immunoassay, either the presence of antigen or the patient's own antibodies (which in some cases are indicative of a disease) can be measured. For instance, when detecting infection the presence of antibody against the pathogen is measured. For measuring hormones such as insulin, the insulin acts as the antigen. Conventionally, for numerical results, the response of the fluid being measured is compared to standards of a known concentration. This is usually done though the plotting of a standard curve on a graph, the position of the curve at a response of the unknown is then examined, and so the quantity of the unknown found. The detection of the quantity of antibody or antigen present can be achieved by either the antigen or antibody.

An increasing amount of biological assays, such as immunoassays and gene expression analysis, are carried out using microarrays, such as DNA microarrays, protein microarrays or antibody microarrays, for example. A microarray is a collection of microscopic spots such as DNA, proteins or antibodies, attached to a substrate surface, such as a glass, plastic or silicon, and which thereby form a "microscopic" array. Such microarrays can be used to measure the expression levels of large numbers of genes or proteins simultaneously. The biomolecules, such as DNA, proteins or antibodies, on a microarray chip are typically detected through optical readout of fluorescent labels attached to a target molecule that is specifically attached or hybridized to a probe molecule. The labels used may consist of an enzyme, radioisotopes, or a fluorophore.

A large number of assays use a sandwich assay format for performing the assay. In this format, a capture probe molecule is immobilized on a surface. In the subsequent steps, a sample solution containing target molecules, also called analytes is applied to the surface. The target or analyte binds in a concentration dependent manner to the capture probe molecules immobilized on the surface. In a subsequent step, a solution containing detection probe molecules is applied to the surface, and the detection probe molecules can then bind to the analyte molecule. The analyte is thus "sandwiched" between the capture probe and detection probe molecules. In some assays, a secondary probe molecule is also applied to the assay, which can bind the detection probe molecule. The secondary probe can be conjugated to a fluorophore, in which case the binding result can be detected using a fluorescence scanner or a fluorescence microscope. In some cases, the secondary probe is conjugated to radioactive element, in which case the radioactivity is detected to read out the assay result. In some cases, the secondary probe is conjugated to an enzyme, in which case a solution containing a substrate has to be added to the surface, and the conversion of the substrate by the enzyme can be detected. The intensity of the signal detected is in all cases proportional to the concentration of the analyte in the sample solution.

Another type of cell and biomolecule separation and detection method uses microfluidic devices to conduct high throughput separation and analysis based on accurate flow controls through the microfluidic channels. By designing patterned fluidic channels, or channels with specific dimensions in the micro or sub-micro scales, often on a small chip, one is able to carry out multiple assays simultaneously. The cells and biomolecules in microfluidic assays are also typically detected by optical readout of fluorescent labels attached to a target cell or molecule that is specifically attached or hybridized to a probe molecule.

However, for protein analysis it remains very challenging to develop multiplexed assays. A number of recent attempts have been made to develop improved multiplexed antibody microarrays for use in quantitative proteomics, and various researchers have begun to examine the particular issues involved. Some of the general considerations in assembling multiplexed immunoassays have been found to include: requirements for elimination of assay cross-reactivity; configuration of multianalyte sensitivities; achievement of dynamic ranges appropriate for biological relevance when performed in diverse matrices and biological states; and optimization of reagent manufacturing and chip production to achieve acceptable reproducibility. In contrast to traditional monoplex enzyme-linked immunoassays, generally agreed specifications and standards for antibody microarrays have not yet been formulated.

The challenge of multiplexed immunoassay is further compounded when using complex biological samples, such as blood and its plasma and serum derivatives or other bodily fluids. The dynamic range of concentration of protein in blood has been found to span 11 orders of magnitude. Thus, when identifying low abundance proteins in blood, it has to be made against a background of proteins 11 orders of magnitude more numerous. As an analogy, if we were to identify a single person among the entire world population it would correspond to less than 10 orders of magnitude, as the world population is still less than 10 billion people.

Immunoassays and other assays exploiting microarrays exploit microfluidics. Microfluidics is concerned with handling and manipulating minute amounts of reagents. A major challenge in microfluidics is the mismatch between conventional liquid handling systems and the small scale of microfluidics, which constitutes a major obstacle to the more widespread adoption of microfluidics in laboratories and clinical settings, and has been described as the "world-to-chip" interface. The difficulty lies in delivering solutions from macroscopic containers such as vials or microplates to the microscopic reservoirs and channels of microfluidics rapidly, and without wastage. The interfacing problem becomes particularly challenging when large numbers of reagents need to be delivered to a microchip. Complex integrated microfluidic circuits have been built using so called multilayer soft lithography, see for example J. M. K. Ng et al in "Components for Integrated Poly(dimethylsiloxane) Microfluidic Systems" (Electrophoresis, Vol. 23, pp 3461-3473), but the delivery of reagents remains cumbersome, and often large external reservoirs with dead volumes are used, multiple tubings need to be manually connected, and reagent loading remains serial, all of which contribute to limit the versatility of these technologies. Many microfluidic chips are still loaded manually using pipettes which is slow, and with a lower limit for the volume of approximately 200 nl, but with little dead volume on the other hand, see for example L. Gervais et al in "Toward One-Step Point-of-Care Immunodiagnostics using Capillary-Driven Microfluidics and PDMS Substrates" (Lab on a Chip, Vol. 9, pp 3330-3337).

Microarrays although typically considered apart from microfluidics also depend on the transfer of minute amounts of reagents. In microarrays, the macro-to-micro challenge was addressed using large number of pins to transfer minute amount of liquids from microtiter plates to chips by repeatedly printing them onto multiple chips to minimize waste. The upload and transfer are controlled by capillary effects that need to be precisely engineered, see for example R. A. George et al in ""Ceramic Capillaries for use in Microarray Fabrication" (Genome Res., Vol. 11, pp 1780-1783) and R. Safavieh et al in "Straight SU-8 Pins" (J. Micromechanics and Microengineering, Vol. 20, 055001, 2010). Inkjet spotters with front-loading have also been developed and used to produce microarrays, see for example H. Li et al in "Hydrogel Droplet Microarrays with Trapped Antibody-Functionalized Beads for Multiplexed Protein Analysis" (Lab on a Chip, Vol. 11, pp 528-534) and M. Pia-Roca et al in "Addressable Nanowell Arrays Formed Using Reversibly Sealable Hybrid Elastomer-Metal Stencils" (Anal. Chem., Vol. 82, pp 3848-3855). The number of nozzles is typically much lower than that for pin spotters, however the programmability and rapid dispensing of droplets on-the-fly compensates for the limited parallelism. More recently, a novel system named the top spot has been presented which is made of a spotting head that is filled using capillary forces and for which dispensing is effected by compression of air above the nozzles, see for example C. Steinert et al in "TopSpot™ Vario: A Novel Microarrayer System for Highly Flexible and Highly Parallel Picoliter Dispensing" (Biomed. Microdevices, Vol. 11, 755-761). This system is overall simpler than inkjet spotters, but lacks individual addressing of the nozzles and requires larger volumes for loading the head. All these systems however remain reliant on robotics and are quite complex.

Recently, several groups proposed novel approaches to transfer minute amounts of reagents by using a "storage chip". In this way, an array can first be formed on one or several chips using high precision inkjet spotters, and subsequently all reagents transferred to another chip, or mixed with a sample, at once. Du, Ismagilov and colleagues have developed an elegant approach called the "SlipChip". With a "SlipChip", nanoliter droplets of reagents are first trapped in channels and recesses which serve as reaction chambers, then a sample is loaded in a microchannel running parallel to the recesses, and then both are merged by sliding the two microstructured chips, see W. Du et al in "SlipChip" (Lab on a Chip, Vol. 9, 2286-2292).

To date, "SlipChips" have been used to deliver a single sample to an array of reagents, such as the delivery of single sample to 48 crystallization wells or to different chambers for sandwich immunoassays, see Du and W. Liu et al in "SlipChip for Immunoassays in Nanoliter Volumes" (Anal. Chem., Vol. 82, pp. 3276-3282), these examples represent a 1-to-N transfer. Alternative chip-to-chip transfer methods based on reagent diffusion from sol-gels and hydrogel spots have recently been proposed in the context of cell-based drug screening. First, the transfer of drugs and drug metabolites from sol-gel spots to cell monolayers on a flat substrate was demonstrated by M. Y. Lee et al in "Metabolizing Enzyme Toxicology Assay Chip (MetaChip) for High-Throughput Microscale Toxicity Analyses" (Proc. Natl. Acad. Sci. U.S.A., Vol. 102, pp. 983-987) and then the transfer from alginate gel droplets to cells encapsulated in collagen by T. G. Fernandes et al in "Three-Dimensional Cell Culture Microarray for High-Throughput Studies of Stem Cell Fate" (Biotechnol. and Bioeng., Vol. 106, pp. 106-118) and M-Y. Lee et al in "Three-dimensional Cellular Microarray for High-Throughput Toxicology Assays" (Proc. Natl. Acad. Sci. U.S.A, Vol. 105, pp. 59-63). More recently, Khademhosseini and colleagues adopted a similar approach to transfer drugs from approximately 200 μm wide posts made of either PDMS in "A Sandwiched Microarray Platform for Benchtop Cell-Based High Throughput Screening" (Biomaterials, Vol. 32, pp. 841-848) or a hydrogel in "Drug-Eluting Microarrays for Cell-Based Screening of Chemical-Induced Apoptosis" (Anal. Chem., Vol. 83, pp. 4118-4125) that were coated or loaded, respectively, with a drug library by inkjet spotting. The library was delivered at once to an array of 400 μm wide micro-wells on a microscope slide by clamping the chips and letting the drug diffuse into the buffer contained in each well. The wells were seeded with cells from a single cell line. This approach allowed selective delivery of a single drug per well, however a minor misalignment persisted possibly due to shrinkage of the PDMS. In summary, for the chip transfer methods described to date, manual alignment based on visible structures on the chip was used, and the transfer followed an N-to-1 or a 1-to-N arrangement with N different reagents being reacted or mixed with a single kind of sample.

In conventional multiplexed sandwich assays in both array and bead formats, the detection antibodies are applied as a mixture, which is much simpler than multi-spotting, but gives rise to interactions among reagents that each constitute a liability for cross-reactivity, which in turn entails lengthy and costly optimization protocols and which severely limits the performance of these assays. Recently, we proposed the antibody colocalization microarray (ACM), see M. Pla-Roca et al in "Antibody Colocalization Microarray: A Scalable Method for Multiplexed and Quantitative Protein Profiling" (submitted to Mol. Cell. Proteomics), which depends on the addressing of each capture antibody spot by a single detection antibody, thus colocalizes each pair and reproducing assay conditions that are found in single-plex ELISA assays, but only requires less than a nanoliter of antibody reagents. The execution of an ACM requires first spotting the capture antibody, removing the slide from the spotter, incubating it with sample, washing and rinsing it as needed, and placing it back for the spotting of the detection antibody followed by binding and incubation. ACM depends on the transfer of N different reagents to N spots each with a different reagent as well, representing an N-to-N transfer. Local addressing was achieved using a custom built microarrayer with precise alignment mechanisms, but unlike approaches with mixing of reagents, spotting needs to be performed as part of the assay, which is cumbersome, and constitutes an obstacle to the adoption of ACM by others.

Here, we present the snap chip for the collective transfer of a microarray of reagents contained within semi-spherical liquid droplets to a target microarray following assembly of the two chips and physical contact of the droplets with the target array. Nanoliters of reagents are spotted on both slides using an inkjet spotter, and selectively transferred from liquid droplets on a transfer chip to an assay chip within the contact areas. A process with back-side alignment and a hand-held snap apparatus were developed to allow for simple and reliable transfer of reagents of an entire microarray. Using the snap chip, we performed multiplexed sandwich immunoassays with colocalization of capture and detection antibodies with 10 targets simultaneously with detection limits in the low pg/ml in buffer and in 10% serum. Finally, we established a protocol for long term storage, three month in this study, of both the assay and transfer chips.

SUMMARY OF THE INVENTION

It is an object of the present invention to provide microarray-to-microarray transfer of reagents for multiplexed sandwich immunoassays.

In accordance with an embodiment of the invention there is provided a method comprising:
providing an assay chip comprising a plurality of first locations disposed on a surface of the assay chip, each first location being a spot comprising at least a capture antibody;
providing a transfer chip comprising a plurality of second locations disposed on a surface of the transfer chip, each second location being a spot comprising at least a detection antibody;
orientating the surface of the assay chip with the plurality of first locations opposite and in predetermined orientation with the surface of the transfer chip with the plurality of second locations;
bringing said surfaces of the assay chip and transfer chip together to within a predetermined spacing;
keeping the assay chip and transfer chip together for a predetermined time; and
separating the assay chip and transfer chip.

In accordance with an embodiment of the invention there is provided a device comprising:
an assay chip comprising a plurality of first locations disposed on a surface of the assay chip, each first location being a spot comprising at least a capture antibody;
a transfer chip comprising a plurality of second locations disposed on a surface of the transfer chip, each second location being a spot comprising at least a detection antibody; wherein
the surface of the assay chip comprising the plurality of first locations is opposite to, in predetermined with, and within a predetermined spacing of the surface of the transfer chip with the plurality of second locations.

In accordance with an embodiment of the invention there is provided a method comprising:
generating a capture antibody chip;
providing a first assay chip comprising a plurality of first locations disposed on a surface of the first assay chip, each first location being a spot comprising at least a capture antibody;
providing a transfer chip;
orientating the surface of the first assay chip with the plurality of first locations opposite and in a first predetermined orientation with the surface of the transfer chip;
bringing said surfaces of the first assay chip and transfer chip together to within a first predetermined spacing;
keeping the first assay chip and transfer chip together for a first predetermined time; and
removing the first assay chip thereby generating the capture antibody chip from the transfer slide with the transferred capture antibodies;
exposing the surface of the transfer chip to a sample for analysis under predetermined conditions;
generating a detection antibody chip;
providing a second assay chip comprising a plurality of second locations disposed on a surface of the second assay chip, each second location being a spot comprising at least a detection antibody;
executing a detection step;
orientating the surface of the detection antibody chip with the plurality of second locations opposite and in a second predetermined orientation with the surface of the capture antibody chip with the transferred capture antibodies;
bringing said surfaces of the second assay chip and transfer chip together to within a second predetermined spacing;
keeping the detection antibody chip and capture antibody chip together for a predetermined time; and
separating the detection antibody chip and capture antibody chip.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

The present invention is directed to bio-analysis and more particularly to a method of providing multiplexed microfluidic analysis via microarray-to-microarray transfer.

Within the following description reference may be made below to specific elements, numbered in accordance with the attached figures. The discussion below should be taken to be exemplary in nature, and not as limiting the scope of the present invention. The scope of the present invention is defined in the claims, and should not be considered as limited by the implementation details described below, which as one skilled in the art will appreciate, can be modified by replacing elements with equivalent functional elements or combination of elements. Within these embodiments reference will be made to terms which are intended to simplify the descriptions and relate them to the prior art, however, the embodiments of the invention should not be read as only being associated with prior art embodiments.

Figure 1:
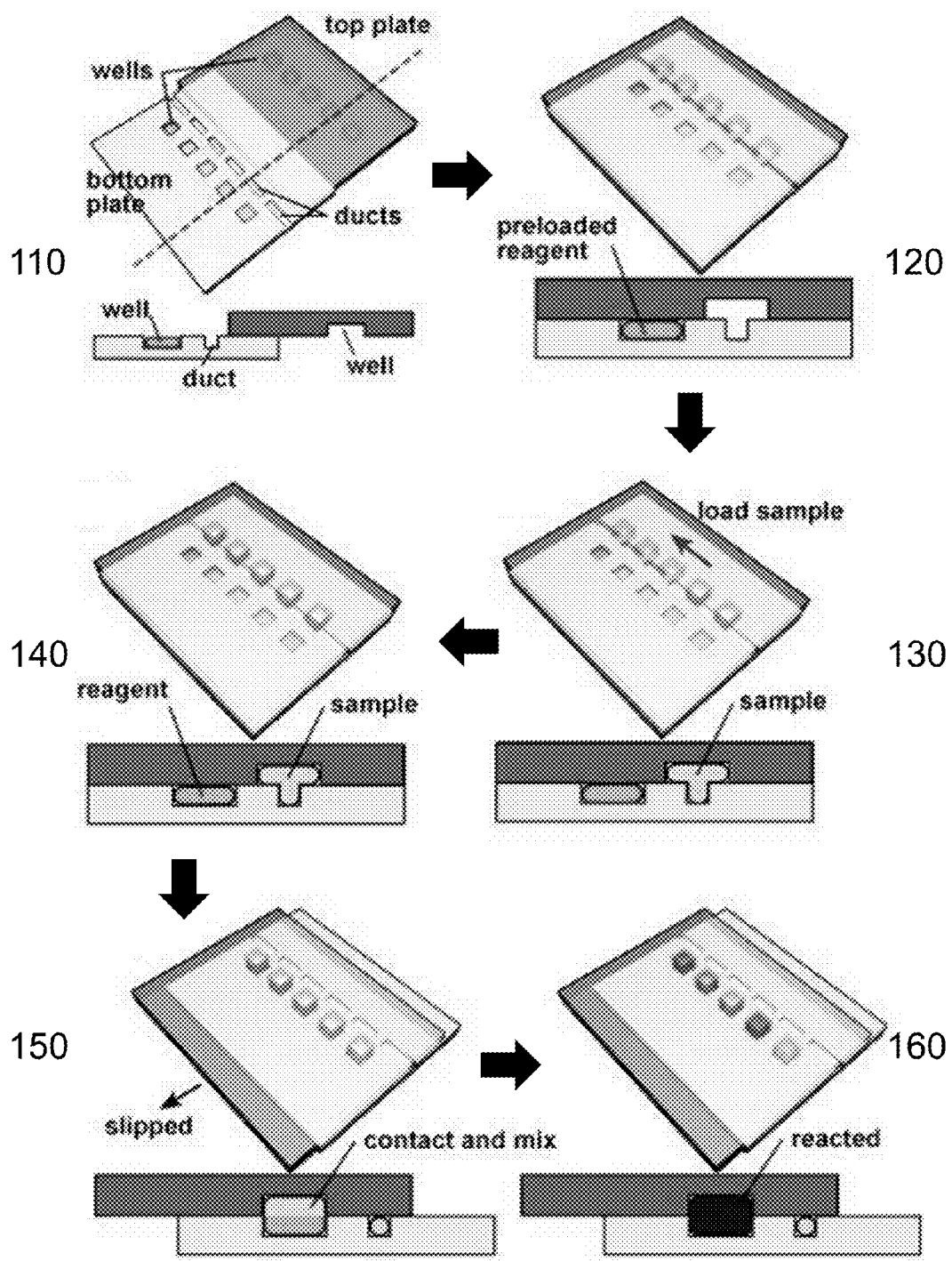
FIG. 1 depicts a "SlipChip" according to the prior art of Du, Ismagilov et al.

Referring to FIG. 1 there is depicted a "SlipChip" according to the prior art of Du, Ismagilov et al in "SlipChip" (Lab on a Chip, Vol. 9, 2286-2292). The SlipChip consists of two plates, but in contrast to the previous methods in the prior art, the two plates are designed to be in contact and are not separated during use. As depicted in FIG. 1 in first assembly 110 the bottom plate contains an array of wells which have been preloaded with reagents. Additionally, the bottom plate contains an array of disconnected ducts that are involved in loading the 'SlipChip". The top plate serves as a lid for the wells of the bottom plate as shown in second image 120 that also contains an array of wells that are complementary in pattern to the array of wells in the bottom plate and connect to the ducts of the bottom plate in a continuous fluidic path. The user receives the chip in the assembled form depicted by second image 120.

The sample is added through the fluidic path provided by the ducts and wells as shown in third and fourth images 130 and 140 respectively. To expose the sample wells to all of the corresponding reagent wells simultaneously the top plate is slipped relative to the bottom plate as shown in fifth image 150. Mixing takes place and the results of the experiments are read out as shown in sixth image 160. Sliding two pieces of a device is common in devices that regulate fluid flow, from a standard high-performance liquid chromatography (HPLC) valve to more sophisticated microfluidic devices, see for example M. Tokeshi et al in "Flow Analysis in Microfluidic Devices" (Chapter 6, oo149-166, published by Wiley) and M. Kuwata et al in "Sliding Micro Valve Injection Device for Quantitative Nano Liter Volume" ($8^{th}$ Int. Conf. Miniaturized Systems for Chemistry and Life Sciences, 2004, pp. 342-344).

In addition, sliding has been used to induce reactions and to induce shear flow in shear-driven chromatography, see for example G. Desmet et al in "The Possibility of Generating High-Speed Shear-Driven Flows and Their Potential Application in Liquid Chromatography" (Anal. Chem., Vol. 72, pp 2160-2165) and Y. Cai et al in "Channel-Free Shear Driven Circular Liquid Chromatography" (Lab on a Chip, Vol. 8, pp. 1784-1786). The "SlipChip" builds on these advances, and the advances in plug-based microfluidics, to provide a platform that delivers controlled volumes of samples to many reaction wells.

Figure 2:
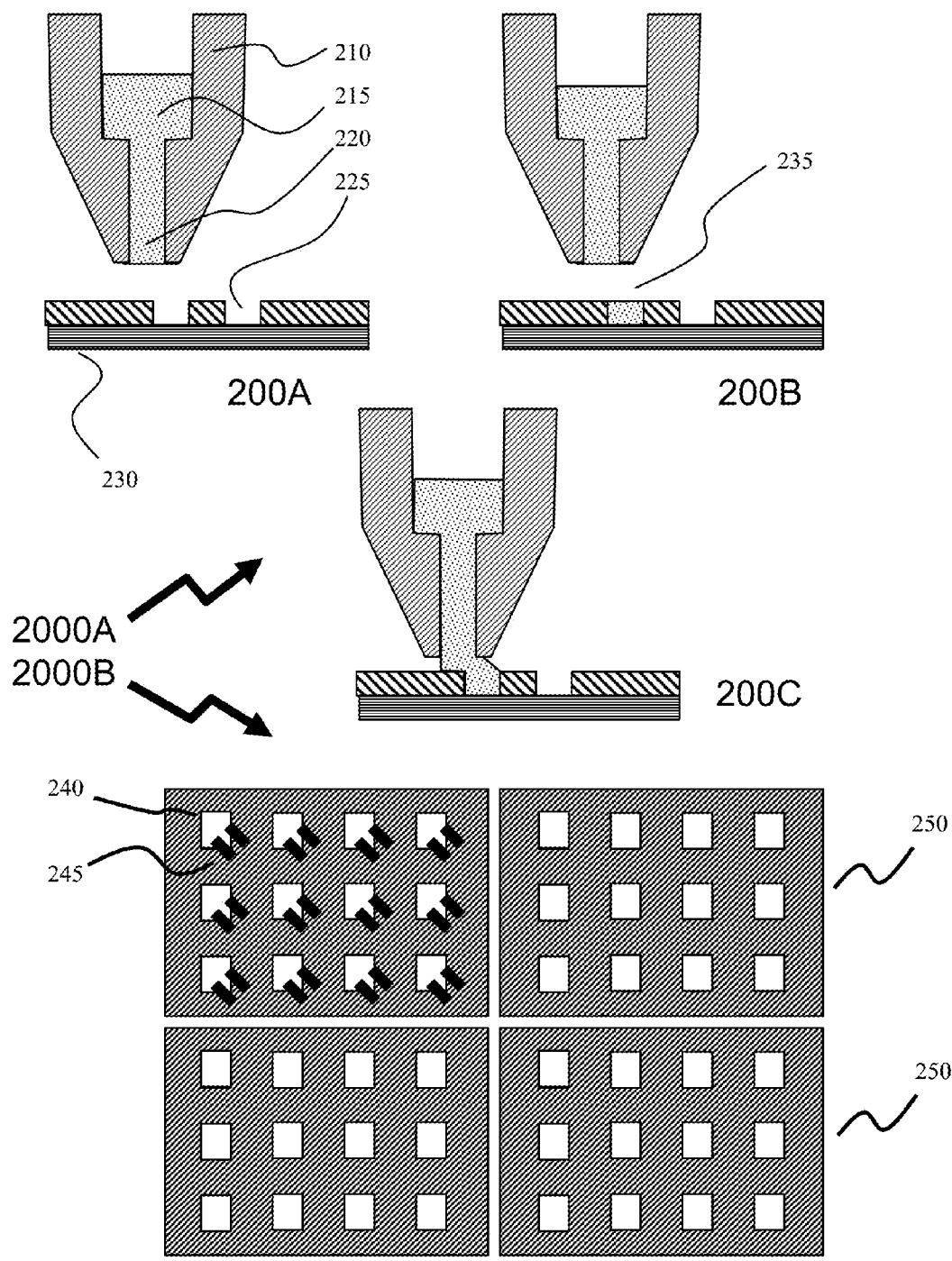
FIG. 2 depicts a microfluidic delivery system for multiplexed analysis according to the prior art of Juncker et al.

Now referring to FIG. 2 there is depicted a microfluidic delivery system 2000A for a single compartment of a microarray and a schematic 2000B of arrayed microfluidic dispensers for use in multiplexed analysis according to the prior art of Juncker et al in US Patent Application 2010/0, 298,163 entitled "Microfluidic Microarray System and Methods for the Multiplexed Analysis of Biomolecules." Referring to first to third stages 200A through 200C respectively, the method and system used to deliver one or more fluid solutions to the micro-compartments of a microarray is shown. As shown in first stage 200A a reservoir or liquid transfer needle 210 of a microfluidic microarray system includes a reservoir which is filled with a liquid 215. The reservoir is in fluid flow communication with, and makes up part of, a fluid conduit 220 defined in the tip of the liquid transfer needle 210. The terms "needle" and "pin" and "capillary" will both be used herein to describe such a liquid transfer needle in a fluid handling and distribution portion of larger microfluidic microarray system of the present invention. The liquid 215 is maintained and thus held back within the fluid conduit 220 by a capillary pressure $P_1$ generated at the interface of the liquid 215 in the reservoir. The needle 210 is located above a microarray 230 having at least one microfluidic micro-compartment 225 defined therein.

Although a variety of different sizes and shapes of the microfluidic micro-compartment 225 are possible, such micro-compartments may for example be approximately between 50 and 150 micrometers (μm) in cross-sectional width (i.e. diameter in the case of a circular micro-compartment well and length or width in the case of a square shaped compartment), and the micro-compartments may be spaced apart by distance substantially corresponding to the cross-sectional width of each of the plurality of micro-compartments (the spacing may however be less than or greater than the individual micro-compartment widths).

Second image 200B shows the transfer of liquid 215 from the reservoir and the fluid conduit 220 into one of the micro-compartments 225. The transfer of fluid takes place automatically upon engagement of fluid flow communication of the needle 210 with the micro-compartment 225, due to a capillary pressure $P_2$ of the micro-compartment 225 which is more negative than the capillary pressure $P_1$ of the reservoir and fluid conduit 220. Although direct contact is not necessary, a defined amount of liquid may be transferred to the micro-compartment upon contact between the liquid transfer needle 210 and the microfluidic micro-compartment 225. Due to the difference in capillary pressures $P_1$ and $P_2$ between the needle 210 and the micro-compartment 225, the liquid 215 within the needle is "sucked" into the micro-compartment 225 until it is filled. When the micro-compartment is filled, it no longer generates a negative capillary pressure, and thus the flow of fluid from the needle to the micro-compartment is automatically interrupted. Upon disengagement of the pin 210 from the surface of the micro-compartment, as shown in third image 200C, the dispensed liquid 235 remains separately in the micro-compartment 225. The same needle 210 can then be used to service multiple such micro-compartments 225 in sequence, until the reservoir is empty.

However, it would be apparent to one skilled in the art that the approach of a single needle whilst an improvement over the state of the art still represents significant time within a microarray system to move the needle across every micro-compartment to dispense the necessary liquid into each. This would be further compounded if multiple liquids were required in a predetermined pattern across a microarray. Juncker, as shown in schematic 2000B, considers this issue and addresses it with an array of needles 245. As shown a plurality of micro-compartment arrays 250 are depicted wherein each comprises a matrix of micro-compartments 240. The microarray system comprises a matching array of needles 245 which can be positioned once and multiple dispensing operations performed concurrently. In principle each needle 245 may be filled with a different liquid. However, whilst reducing the number of needle placement and dispensing steps the process now places increased fabrication and assembly tolerances on the array of needles 245 to ensure that these all make contact with the micro-compartments 240 as required and that no cross-contamination arises from misalignment of the needles 245 relative to the micro-compartments 240.

Experimental Materials:

Within the descriptions of experiments presented below using microarray-to-microarray transfer equipment according to embodiments of the invention different materials were employed. For multiplexed microfluidic analysis rabbit anti-goat immunoglobulin G (IgG) (H and L chains, referred to as H+L) labeled with the fluorescent dye Alexa Fluor 488 and goat anti-mouse IgG (H+L) labeled with Alexa Fluor 647 were employed. Antibody and antigen pairs used included human epidermal grow factor receptor 2 (HER 2), Endoglin (ENG), Leptin (LEP), fibroblast growth factor (FGF), osteopontin (OPN), tumor necrosis factor receptor-II (TNF RII), granulocyte macrophage colony-stimulating factor (GM-CSF), chemokine (C-C motif) ligand 2 (CCL 2), chemokine (C-C motif) ligand 3 (CCL 3), interleukin-1 beta (IL 1β), and labeled streptavidin Cy 5. Other materials included phosphate buffered saline (PBS), Tween-20 (polysorbate 20 which is a surfactant and spreading agent), bovine serum albumin (BSA), and normal human female serum (single donor), and BSA-free StabilGuard® Choice Microarray Stabilizer. Slides were coated with either nitrocellulose or aminosilane.

Scanning and Analysis:

Within the experiments presented below a commercial microarray laser scanner (LS Reloaded™ by Tecan) was used to scan slides. For the one-step assays, a 488 nm and 633 nm laser were used simultaneously to image capture antibody spots and the transferred proteins. For sandwich assays, only the 633 nm laser was used. The fluorescence intensity was computed by subtracting the background signal in the vicinity of each spot. All the experiments were performed in triplicate, and the data was analyzed using analysis software (Array-Pro Analyzer) and graphics were produced with graphical software (SigmaPlot). The lower limit of detection (LOD) of the sandwich assays were calculated from the negative controls without antigen incremented by three times the standard deviation between three independent assays.

Figure 3A:
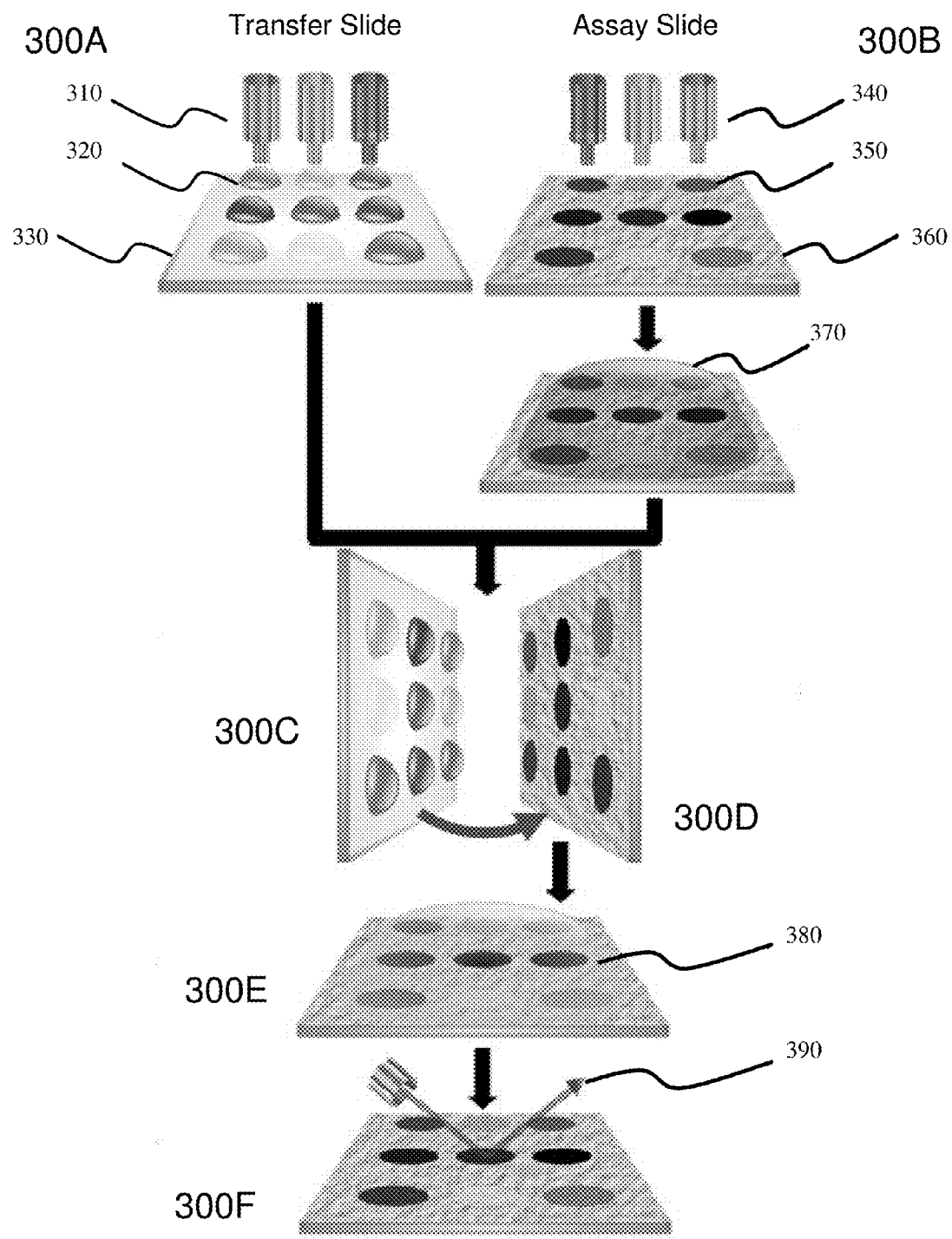
FIG. 3A depicts a process flow for microarray-to-microarray transfer of reagents for multiplexed sandwich immunoassays according to an embodiment of the invention.

Microarray Fabrication:

The procedure for the microarray-to-microarray transfer using snap chips for conducting multiplex immunoassays with colocalization of each capture and detection antibody pair is shown in FIG. 3A according to an embodiment of the invention. Capture antibodies 350 are spotted onto an assay chip 360 using inkjets 340 to form a first matrix as shown in first step 300B. Similarly, biotinylated detection antibodies 320 are spotted onto a transfer chip 330 using inkjets 310 to form a second matrix as shown in second step 300A. For example a glass slide with an approximately 10 μm thick nitrocellulose coating may be used as assay chip 360 as the three-dimensional structure of the nitrocellulose provides a high antibody binding capacity, and will in subsequent steps absorb the solution from the transfer chip 330.

For the transfer chip 330 native glass slides whilst possible typically yield liquid droplets that tend to spread out on the hydrophilic glass thereby forming a thin layer that impacts the subsequent transfer step. A glass slide with hydrophobic coating typically yields rounded droplets which help ensure fluidic contact to the assay chip 360 during the transfer operation, but for the diameters used here, required large volumes of liquid. Within initial experiments employing the microarray-to-microarray transfer method of the invention larger diameters were selected for the droplets on the transfer chip 330 as these allowed for relaxed the alignment constraints while ensuring complete overlap between the capture antibody spot and biotinylated detection antibody spot.

Within the experiments reported in this specification using an embodiment of the invention glass slides with an aminosilane coating with an intermediate contact angle of approximately 65° were used for the transfer chip 330. These afforded a suitable compromise between a rounded droplet while reducing the volume required, see R. Briard et al in "Crack Bridging Mechanism for Glass Strengthening by Organosilane Water-based Coatings" (J. Non-Cryst. Solids, Vol. 351, pp. 323-330). The assay chip 360 may then be incubated with a protective coating 370.

Once fabricated the spotted transfer chip 300C and spotted incubated assay chip 300D were transferred to the snapping system as described below in respect of FIGS. 4 and 5. Following snapping and separation, droplets were visible on the nitrocellulose coating of the spotted assay chip 300D, but no or very little residue was visible on the aminosilane coating of the spotted assay chip 300C, indicating that the transfer was both reliable and efficient. Next the combined slide 300E is incubated, for example with streptavidin-Cy5 380 before being characterized with laser fluorescence based test system giving emitted fluorescence 390.

Accordingly, for experiments reported below in respect of microarray-to-microarray snap fit processes typical processes and parameters for preparing the slide based microarrays were as follows. For the assay chip, such as assay chip 300B in FIG. 3A, capture antibody solutions containing 400 μg/ml antibodies and 10% glycerol in PBS were spotted on a nitrocellulose slide at a relative humidity of approximately 60%, each spot containing approximately 1.2 nl. Detection antibody solutions containing 20 μg/ml antibodies, 20% glycerol, and 1% BSA were spotted on an aminosilane slide to form the transfer chip at a relative humidity of 80% to prevent evaporation; each spot contained approximately 8 nl. Spotting was performed using an inkjet spotter (Nanoplotter 2.0 by GeSiM). The center-to-center spacing between spots was 800 μm for a large scale array, and 1 mm for an assay although it would be apparent that other values may be employed.

After spotting, an assay chip was typically incubated for 1 hour at room temperature with a humidity of 60%. A slide module gasket with 16 modules (Grace Bio-Labs Inc.) was clamped on the slide dividing it into 16 wells for immunoassays. After incubation the assay chip was rinsed twice with PBS containing 0.1% Tween-20 (PBST) for 5 min on a shaker at 450 rpm and once with PBS for 5 min on the shaker at 450 rpm.

Figure 3B:
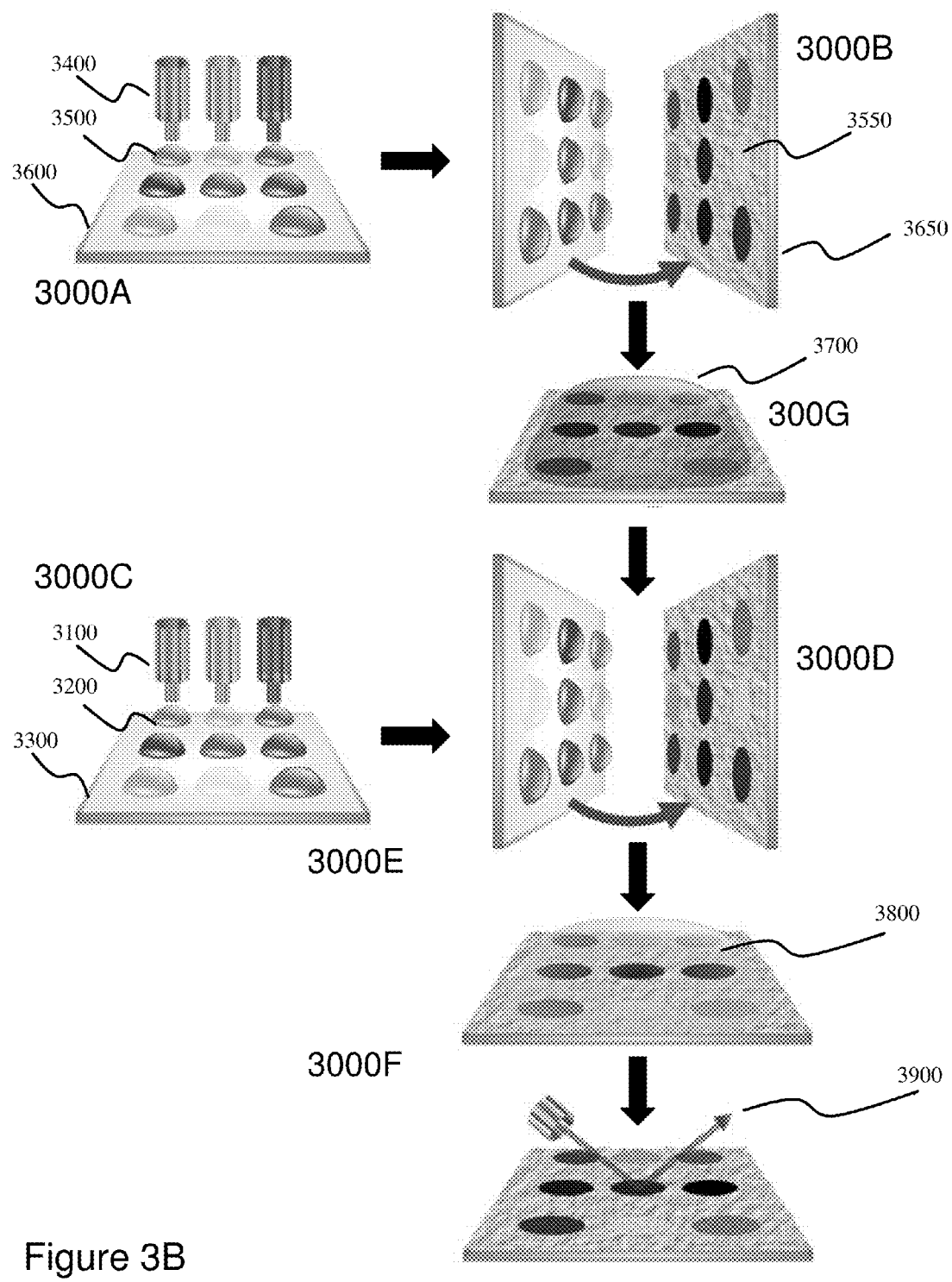
FIG. 3B depicts a process flow for microarray-to-microarray transfer of reagents for multiplexed sandwich immunoassays according to an embodiment of the invention.

Now referring to FIG. 3B there is depicted a procedure for the microarray-to-microarray transfer using snap chips for conducting multiplex immunoassays with colocalization of each capture and detection antibody pair according to an embodiment of the invention. Capture antibodies 3500 are spotted onto a first transfer chip 3600 using inkjets 3400 to form a first matrix as shown in first step 3000A. These are then transferred to an assay slide 3650 to form a matrix of transferred capture antibodies 3550 in second step 3000B. For example, first transfer chip 3600 may be a glass slide with an aminosilane coating with an intermediate contact angle of approximately 65°. The assay slide 3650 with transferred capture antibodies 3550 may then be incubated with a protective coating 370 in third step 3000G.

Next, detection antibodies 3200 are spotted onto a second transfer chip 3300 using inkjets 3100 to form a second matrix as shown in fourth step 3000C. For example a glass slide with an approximately 10 μm thick nitrocellulose coating may be used as assay chip 360 as the three-dimensional structure of the nitrocellulose provides a high antibody binding capacity, and will in subsequent steps absorb the solution from the second transfer chip 3300. For the second transfer chip 3300 a glass slide with hydrophobic coating is typically employed to yield rounded droplets which help ensure fluidic contact to the assay slide 3650 during the transfer operation, but for the diameters used here, required large volumes of liquid. Within initial experiments employing the microarray-to-microarray transfer method of the invention larger diameters were selected for the droplets on the second transfer chip 3300 as these allowed for relaxed the alignment constraints while ensuring complete overlap between the capture antibody spot and biotinylated detection antibody spot.

Once fabricated the spotted second transfer chip 3300 and spotted incubated assay chip 3650 were transferred to the snapping system as described below in respect of FIGS. 4 and 5A to perform fifth step 3000D. Following snapping and separation, droplets were visible on the nitrocellulose coating of the spotted assay chip 3650, but no or very little residue was visible on the aminosilane coating of the spotted second transfer chip 3300, indicating that the transfer was both reliable and efficient. Next the combined slide was is incubated in sixth step 3000E, for example with streptavidin-Cy5 3800 before being characterized with laser fluorescence based test system in the seventh step giving emitted fluorescence 3900.

Accordingly using the procedure described above in respect of FIG. 3B the inventors employed a commercial inkjet spotter to spot 0.65% alginate solutions mixed with cAb-coated polystyrene microbeads onto aminosilane slides at precise coordinates, and fluorescently labeled dAbs in a 1% agarose solution on another slide in a mirrored pattern. The alginate cAb droplets were gelated immediately by adding a calcium solution and the agarose dAb droplets by cooling the slide to 4° C. Next, the cAb slide was blocked with bovine serum albumin for 1 h, and incubated with a sample for 1 h, and briefly dried. The two slides were then clamped together using the snapping system presented below in respect of FIGS. 4 and 5 before the combined slide was incubated for 1 hour and read out using a microarray scanner.

Microarray-to-Microarray Mirror Alignment:

In order to ease the microarray-to-microarray transfer minor patterns and alignment markers are provided on the assay chip and transfer chip according to some embodiments of the invention where visual alignment of the assay chip/ transfer chip alignment is made. As indicated in FIG. 4 during the spotting process 4000A, the bottom right corner of each slide is pressed against a mechanical stop 470 on the slide deck. However, during the transfer process 4000B the two slides face one another and for the transfer chip, the bottom-right corner becomes the bottom-left corner. Typically, the position of the spots on the slides is not absolute, but relative to the first spot and to the corner to which the slide was aligned, which is suitable for most applications, but not for snap chip applications because minor alignment is performed relative to an opposite corner. The alignment following mirroring is further complicated by the fact that in most inkjet spotting systems the inkjets do not spot perfectly straight, and that the size of the glass slides is not accurate as these are mass produced consumable items, and that it would thus not be possible to align the spots by aligning the assay chip to the bottom-right and the transfer chip to the bottom-left corner.

Two approaches have been considered for achieving the required overlay accuracy during the transfer process 4000B. Within the first approach the spots were provided at exact coordinates in a minor pattern on both slides and then each slide aligned relative to the bottom-left edge on each moiety of the snap system. The second approach was to spot an alignment mark on the back-side of the transfer side, having predetermined relationship to the rightmost spot of the top row of the assay chip, while aligning it relative to the bottom right corner, flip it, align it again relative to the bottom right corner and use the image recognition system of the inkjet to align the first spot exactly atop the alignment mark.

This second approach being shown by first to third schematics 400A through 400C respectively in spotting process 4000A in Figure B. In this manner, both slides will be aligned to the same edge (i.e. bottom right when seen from the top) and the alignment accuracy is independent on the size of the slides. Within the experiments presented within this specification the second approach was employed. Accordingly as shown by first schematic 400A an assay chip 420 is patterned with capture antibody spots 430 using inkjet(s) 410. The back of the transfer chip 440 is patterned with the reference spot 450 in second schematic 400B whilst in third schematic 400C the front side of the transfer chip 440 is shown with reference spot 450 visible through the transfer chip 440 whilst the detection antibody spots 460 are disposed on the transfer chip 440 using inkjet(s) 410. Assembly process 4000B in FIG. 4 depicts the assay chip 420 and front side of transfer chip 440 ready for assembly with the axis of symmetry between them.

Figure 4:
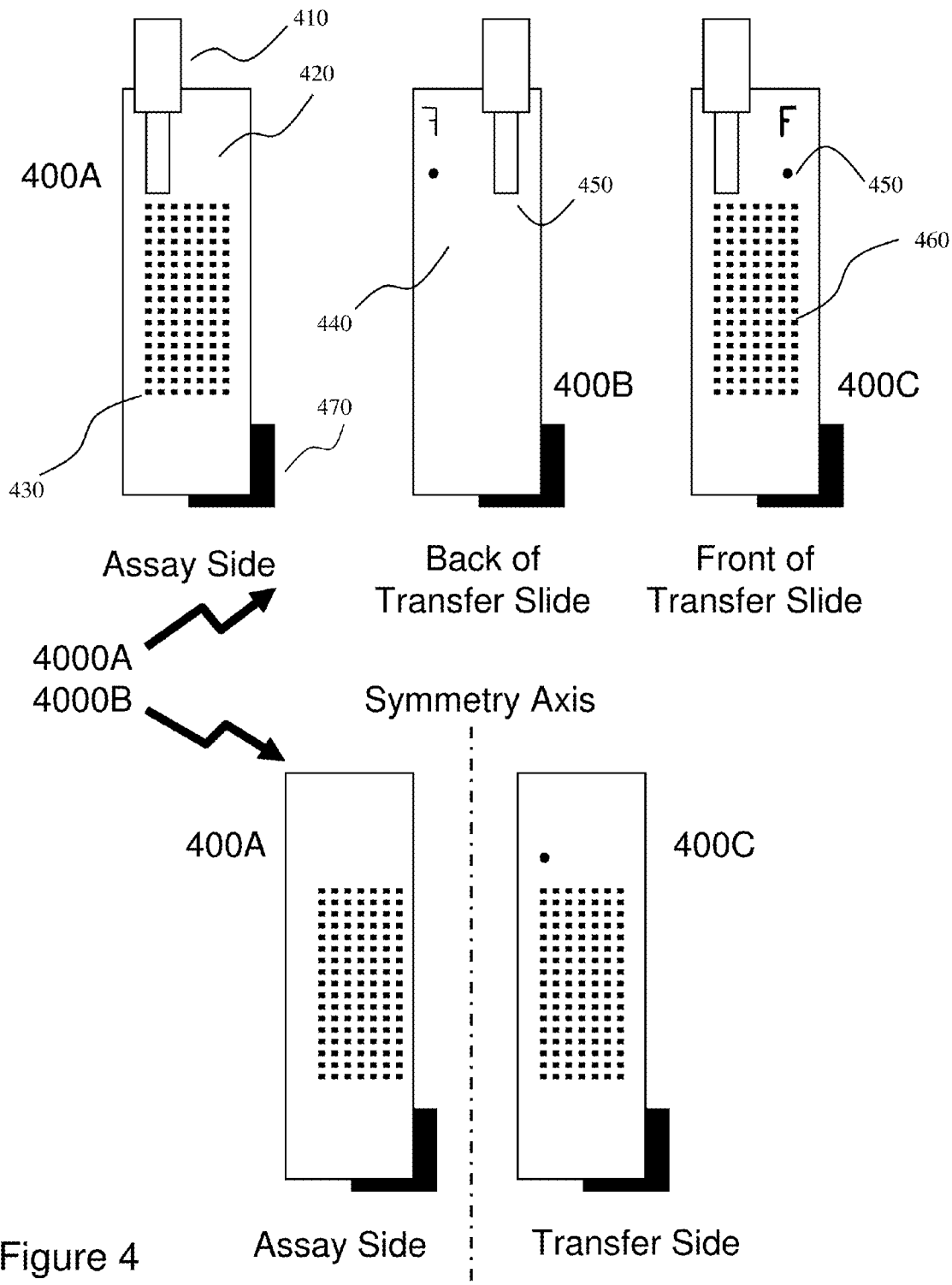
FIG. 4 depicts a protocol for minor alignment and schematics for microarray-to-microarray transfer of reagents for multiplexed sandwich immunoassays according to an embodiment of the invention.
Figure 5A:
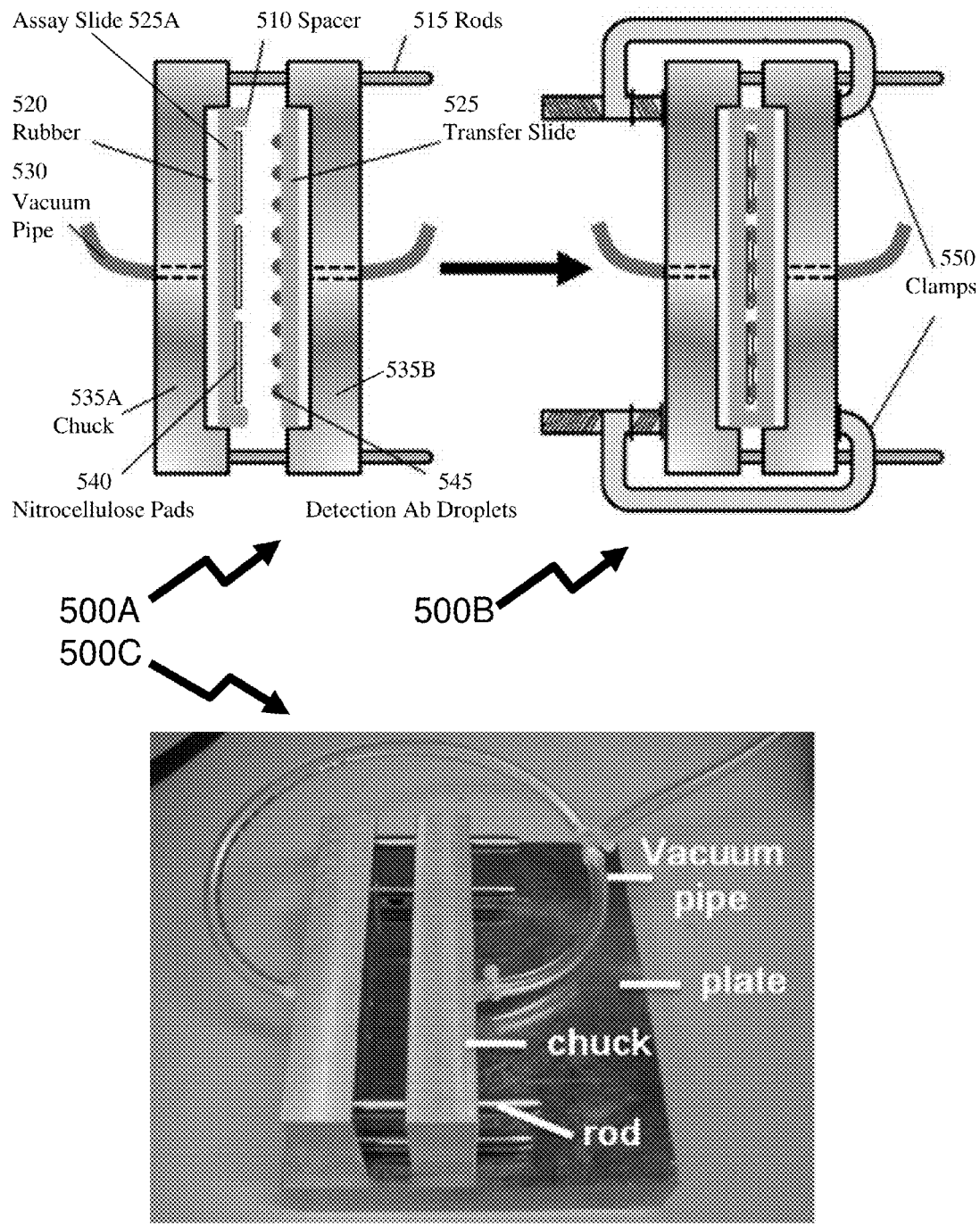
FIG. 5A depicts a first mechanical structure for snap assembly and microarray-to-microarray transfer of reagents for multiplexed sandwich immunoassays according to an embodiment of the invention.

Snapping of Microarray Slides:

The assay chip, such as assay chip 400A in FIG. 4, and the transfer chip, such as transfer chip 400C in FIG. 4, according to an embodiment of the invention are placed in a snap apparatus, shown in open state 500A and closed 500B in FIG. 5A together with optical micrograph 500C. As shown the snap apparatus comprises comprising first precision milled vacuum chuck 535A, second precision milled vacuum chuck 535B, and four steel rods 515. Each of the first and second precision milled vacuum chucks 535A and 535B respectively comprise a recess for inserting and aligning the assay and transfer chips and serve to hold them in place prior to snapping them together. To keep the precise minor symmetric pattern alignment between the two slides, the assay chip 525A and the transfer chip 525B are pushed against the bottom right corner and the bottom left corner in the recess of their respective vacuum chucks. The four steel rods 515 are fixed to the first precision milled vacuum chuck 535A and serve to guide the second precision milled vacuum chuck 535B which has four holes matching the pattern of the steel rods 515 assembled into the first precision milled vacuum chuck 535A. A steel plate, shown in optical micrograph 500C, is used according to an embodiment of the invention during snapping to support the first and second precision milled vacuum chucks 535A and 535B respectively whilst they were being manually clamped together with clamps 550.

The first and second precision milled vacuum chucks 535A and 535B are clamped to at predetermined pressure. Kapton spacers 510 with a thickness of approximately 25 µm were placed between the assay chip 525A and transfer chip 525B to provide control of the gap between them during clamping and to avoid excessive "squeezing" of the droplets during snapping. A typically clamping duration being one minute. Approximately 500 µm thick rubber cushions 520 were inserted between each of the assay chip 525A and transfer chip 525B and their respective one of the first and second precision milled vacuum chucks 535A and 535B accommodate small imperfections and improve pressure distribution the pressure across the slides. Following snapping, a liquid bridge between the assay chip 525A and transfer chip 525B is established, and the detection antibody droplets 545 and associated reagents were transferred to the assay chip 525A from the transfer chip 525B upon subsequent separation. As shown assay chip 525A also shows the nitrocellulose pads 540.

It would be evident that the snap apparatus as depicted in FIG. 5A may be varied without departing from the scope of the invention. For example, the clamping process may be automated, additional alignment verification means incorporated such as providing contacts on the assay chip and transfer chip such that only in correct alignment will all such contacts provide electrical connections, and that the chucks may be machined from optically transparent materials allowing with suitable absorber materials other than rubber the visual alignment of the slides prior to confirming the snap operation.

Figure 5B:
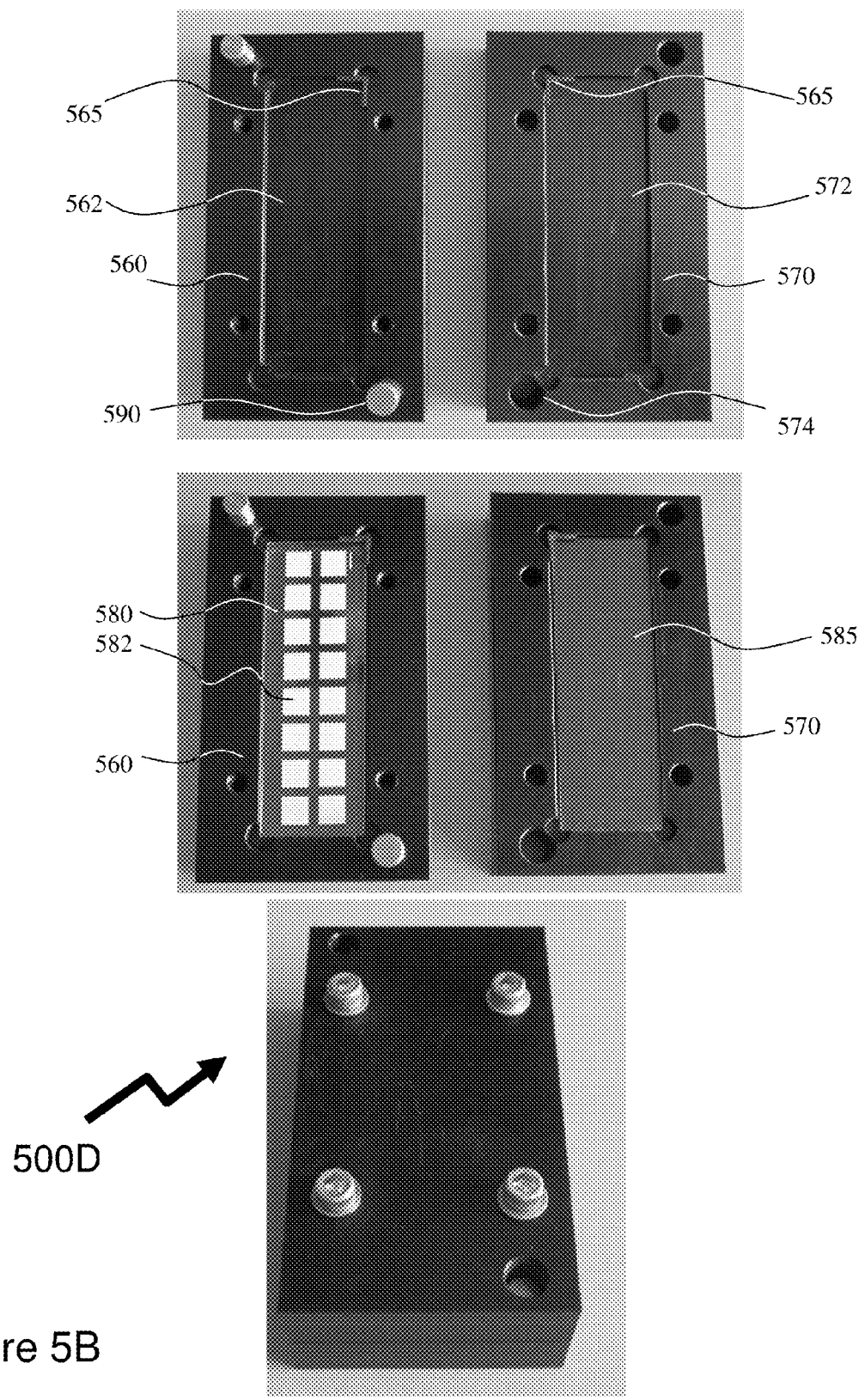
FIG. 5B depicts a second mechanical structure for snap assembly and microarray-to-microarray transfer of reagents for multiplexed sandwich immunoassays according to an embodiment of the invention.

Now referring to FIG. 5B there is depicted a second mechanical structure for snap assembly and microarray-to-microarray transfer of reagents for multiplexed sandwich immunoassays according to an embodiment of the invention. In contrast to the snap apparatus, shown in open state 500A and closed 500B in FIG. 5A together with optical micrograph 500C the second mechanical structure comprises base and cover elements 560 and 570 respectively made from polyoxymethylene (POM). POM offers high mechanical stiffness, good machining characteristics, and excellent mechanical stability under 40° C. Base and cover elements 560 and 570 reduce the overall dimensions to approximately 98 mm×55 mm×30 mm and weight to approximately 232 g. Formed within base element 560 is a first recess 562 and posts 590 are inserted into holes machined within the base 560. A second recess 572 is formed within cover element 570 together with machined holes 574 to accept the posts 590 when the cover element 570 is flipped and aligned to the base element 560.

Subsequently the assay slide 582 with patterned nitrocellulose pads 582 is assembled into the base element 560 and is retained through pressure from a rubber element 565 inserted within the recess 562 of the base element 560.

Similarly the transfer slide 585 is retained through pressure by a rubber element 565. Accordingly inversion of one or other of assay slide 582 and transfer slide 585 within their respective base or cover elements 560 and 570 respectively and engagement of the base and cover elements 560 and 570 respectively via posts 590 and holes 574 provides the desired flip-chip process as described above in respect of FIGS. 3A through 5A respectively. Maintenance of the engagement of the base and cover elements 560 and 570 respectively is achieved through four screws as depicted in assembled unit image 500F. It would be evident to one skilled in the art that variants of the design described above in respect of FIG. 5B may be implemented without departing from the scope of the invention.

Figure 5C:
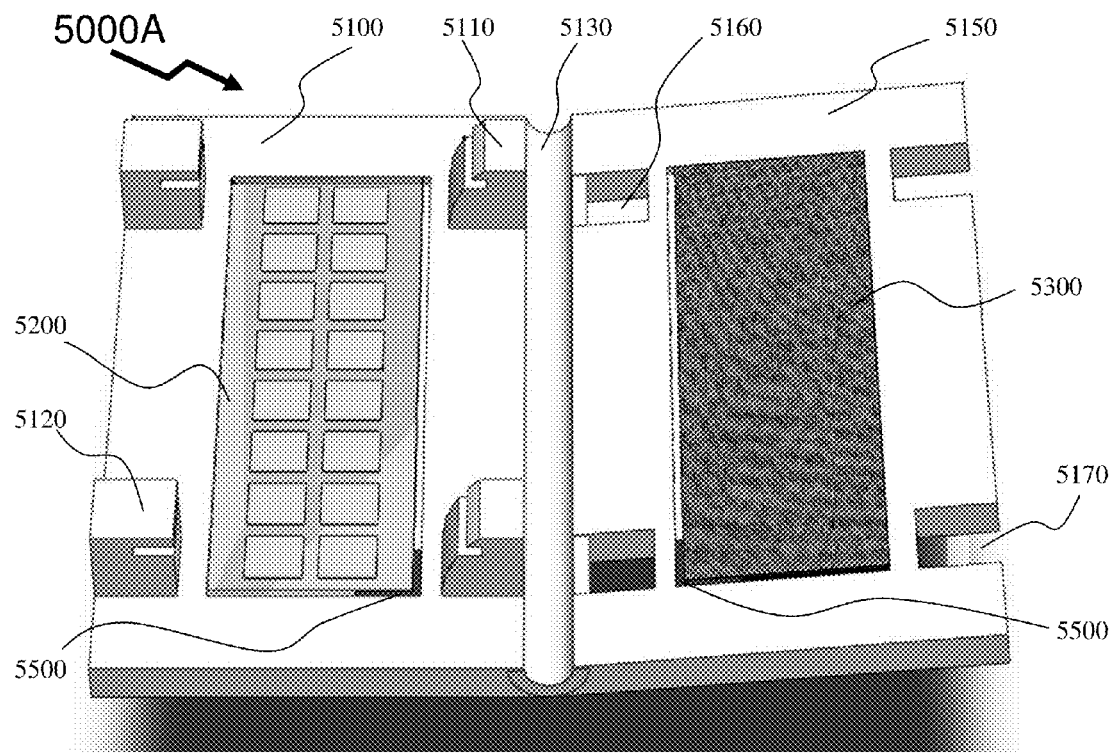
FIGS. 5C and 5D depict third and fourth mechanical structures for snap assembly and microarray-to-microarray transfer of reagents for multiplexed sandwich immunoassays according to an embodiment of the invention.
Figure 5C:
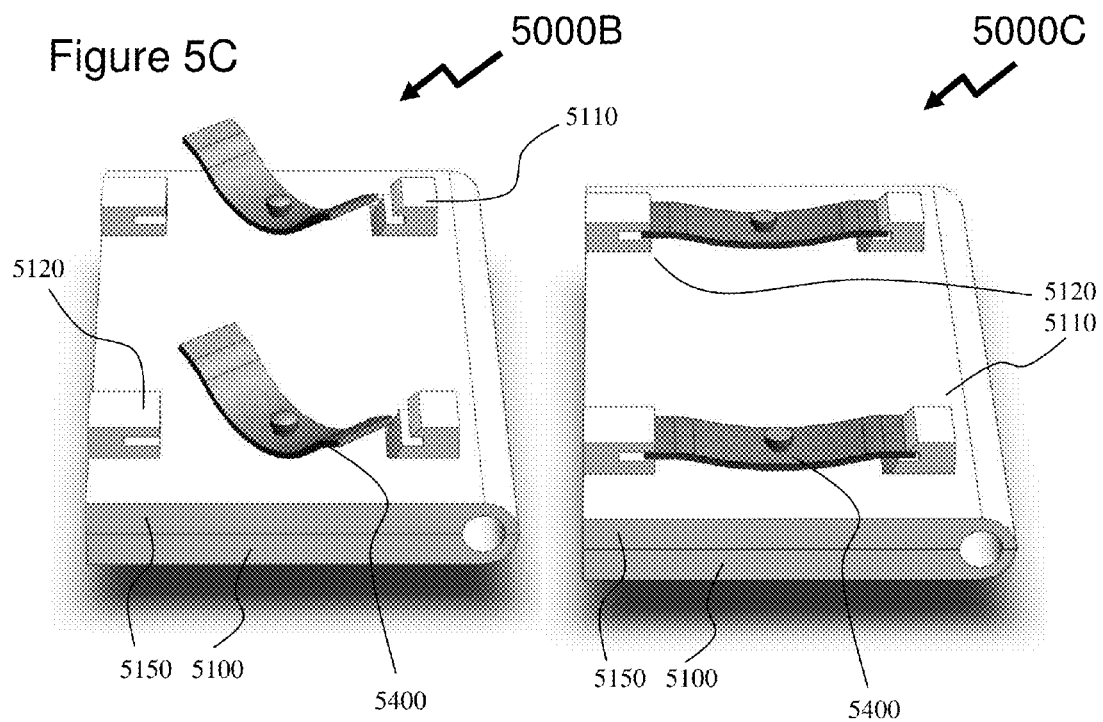
Figure 5D:
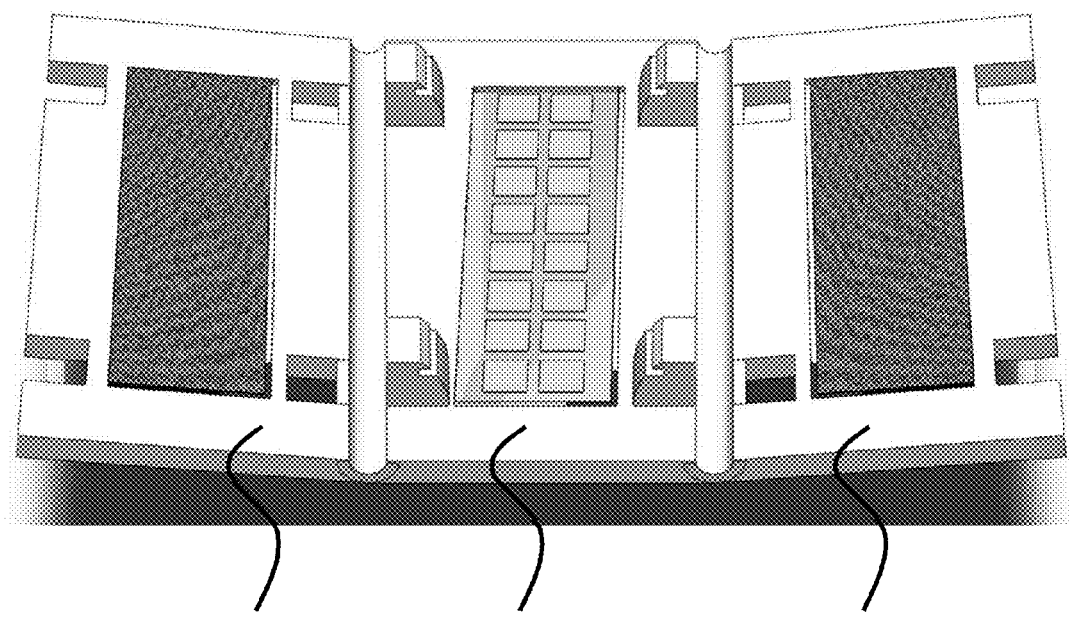

However, in some instances rather than clinical type environments, or even in such environments, it would be beneficial to have a disposable snap-chip design that allows for high volume, low cost manufacturing through injection molding for example. Such an approach is depicted in FIG. 5C wherein a third mechanical structure for snap assembly and microarray-to-microarray transfer of reagents for multiplexed sandwich immunoassays according to an embodiment of the invention is presented. Accordingly, a clam shell comprising base 5100 and cover 5150 joined by a hinge 5130 is depicted wherein base 5100 has a first recess for holding the assay chip 5200 and cover 5150 has a second recess for holding the transfer slide 5200. The assay chip 5200 and transfer slide 5300 being retained and positioned via rubber elements 5500. Accordingly closure of the cover 5150 over the base 5100 aligns the assay chip 5200 and transfer slide 5300 by virtue of first and second pairs of pillars 5120 and 5110 respectively engaging first and second pairs of holes 5170 and 5160 respectively.

The base 5100 and cover 5150 being held in position by spring loaded retainer clips 5400 which engage slots within each of the first and second pairs of pillars 5120 and 5110 respectively as depicted by closed and locked configuration schematics 5000B and 5000C respectively. It would evident that other closures may be employed without departing from the scope of the invention wherein these provide pressured contact to ensure interfacing of the transfer slide 5300 and the assay chip 5200. It would also be evident that clear materials compatible with injection molding such as polymethyl methacrylate (PMMA) may be employed to allow alignment and engagement of the transfer slide 5300 and assay chip 5200 to be visualized as they are performed. Further, as presented schematically in FIG. 5D a three element assembly may be employed such that a base 52 has hinged connections to first cover 51 and second cover 53. First cover 51 may for example support the transfer slide whereas the second cover 53 supports a slide with streptavidin-Cy5 3800 for example such that the assay chip 5200 in base 52 may be incubated and then characterized with a laser fluorescence based test system.

Accuracy of Microarray-to-Microarray Transfer:

We characterized the alignment accuracy for 256 spots arrayed over a slide, 16 spots on each of the 16 nitrocellulose pads, by spotting and transferring IgGs labeled with two different fluorescent dyes respectively and scanning the nitrocellulose slide immediately after transferring. The average center-to-center distance between the spots following transfer to the assay chip was 147 μm, with the largest distance being 216 μm. We observed a position shift from the left to the right side of the slide during spotting, which doubled following mirrored transfer, indicating that there was an angular misalignment between the slide deck and the motorized inkjet stage. To achieve complete overlap between corresponding spots, each capture spot was serviced with 1.2 nl of solution yielding a 300 μm spot on the nitrocellulose slide, while 8 nl of detection antibody solution were applied and produced a droplet that was 700 μm in diameter on the transfer chip.

Figure 6A:
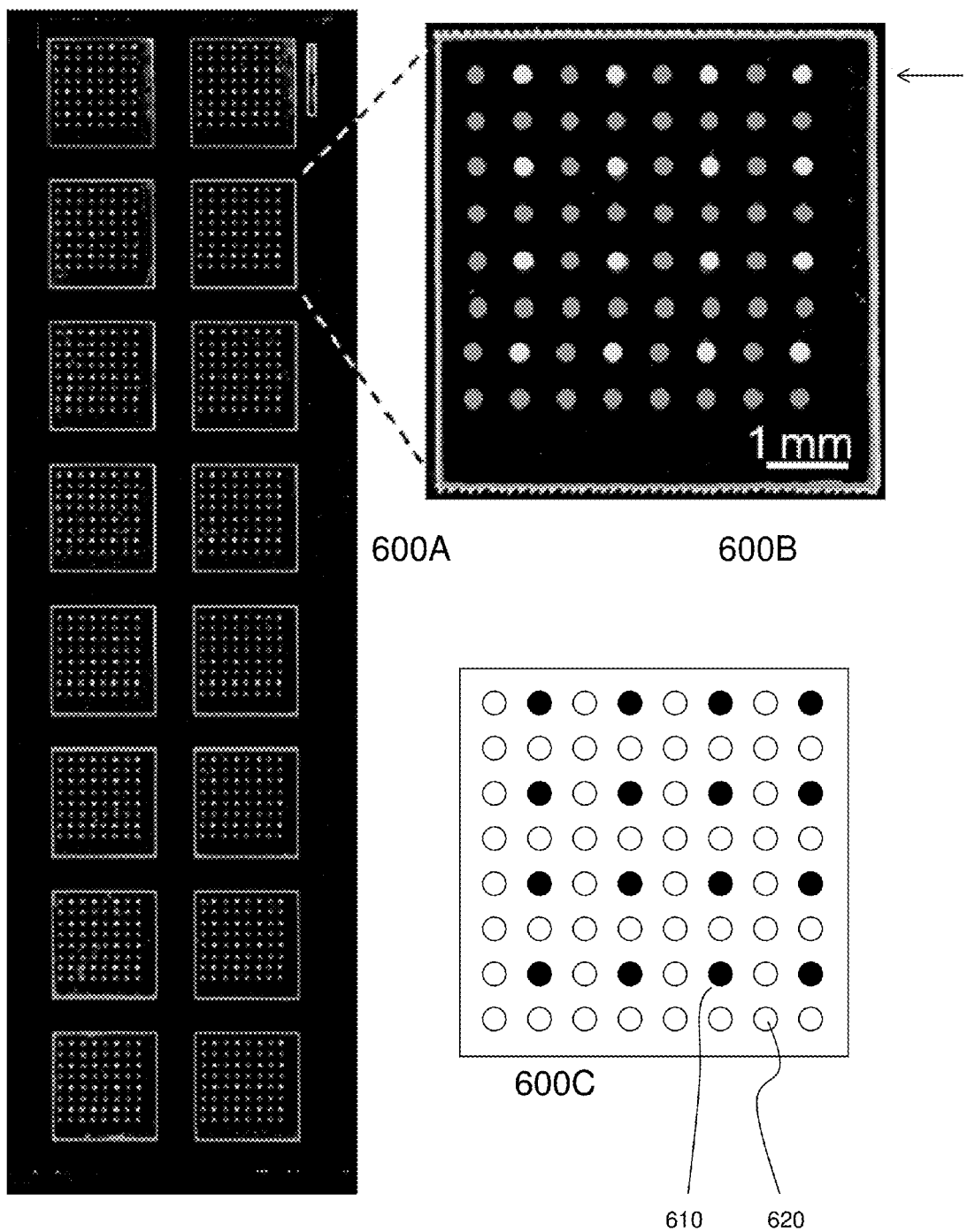
FIG. 6A depicts fluorescence images of assay chip after snapping and transfer according to an embodiment of the invention.

Microarray-to-Microarray Transfer of Antibody Reagents:

The inventors have evaluated the use of the snap chip for implementing immunoassays. An array of 256 fluorescent IgGs was transferred from a transfer chip to an assay chip patterned with an array of 1024 fluorescent anti-IgGs as shown in optical micrograph 600A in FIG. 6. 20% glycerol was added to the detection buffer to prevent drying of the detection antibodies while the assay chip was dried under a stream of nitrogen prior to the transfer to promote the absorption of the detection antibody droplets in the nitrocellulose while minimizing lateral spreading. Visual inspection reveals a selective and homogeneous transfer of proteins across the entire slide as shown in optical micrograph 600B for one 64 array of fluorescent anti-IgGs of the 1024 fluorescent anti-IgGs. The fluorescence intensity profile of the two proteins in the one-step assay show excellent overlap in the spot locations as evident in FIG. 6B.

Figure 6B:
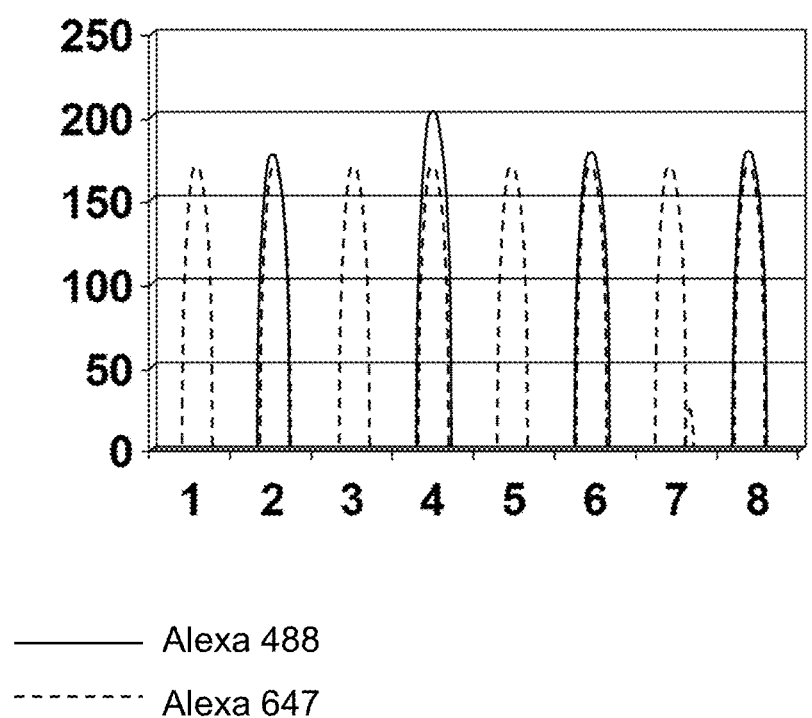
FIG. 6B depicts measured intensity profiles for the fluorescence from the spots within a row of one array in the assay chip of FIG. 6A.

The 1024 array of anti-goat IgGs were labeled with Alexa 488 (green) and spotted on centre-to-centre spacing of 800 μm whilst the 256 array of goat IgGs were labeled with a centre-to-centre spacing of 1600 μm. Intermediate spots were loaded with a solution of PBS. In optical micrograph 600A the square borders represent the edges of the 16 nitrocellulose pads disposed on the glass slide. Fluorescence intensity profiles of the green (Alexa 488) and red (Alexa 647) protein spots in the row marked by the arrow in optical micrograph 600B are shown in FIG. 6B.

Figure 6C:
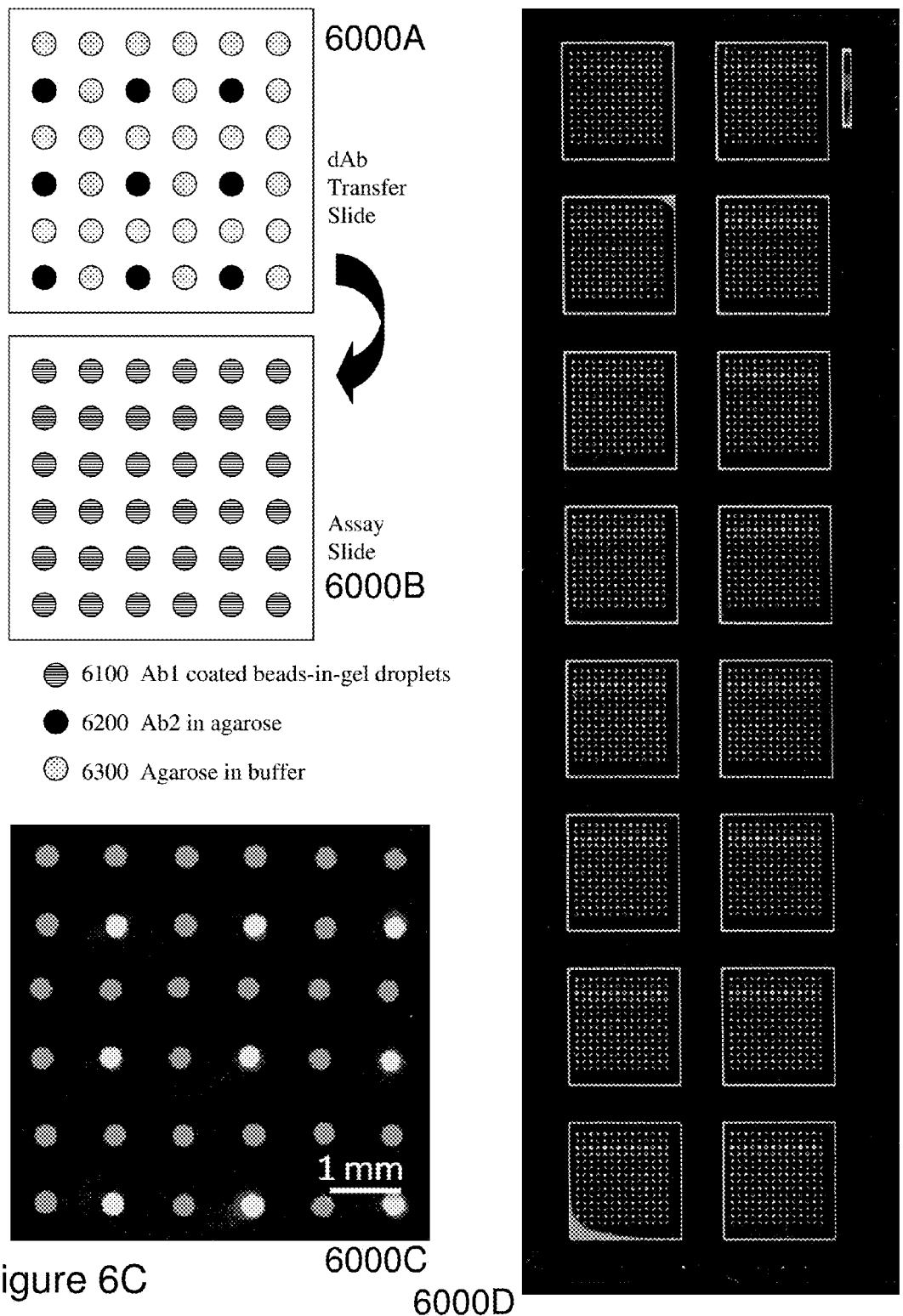
FIG. 6C depicts fluorescence images of a high density assay chip after snapping and transfer according to an embodiment of the invention.

Now referring to FIG. 6C there is depicted a schematic showing dAb transfer slide 6000A and assay slide 6000B. The assay slide 6000B comprising Alexa 532 labeled goat IgG (Ab 1) antibodies coated to beads (Ab 1 coated beads-in-gel droplets 6100). The dAb transfer slide 6000A comprising agarose solution in buffer (Agarose in buffer 6300) and Alexa 633 labeled anti-goat IgG (Ab 2) antibodies dissolved in agarose solution and spotted to every second spot in every second row (Ab2 in agarose 6200). It would be evident to one skilled in the art that the performance of multiplexed assays is severely limited owing to cross-reactivity between antibodies and antigens which occurs because detection antibodies are applied as a mixture.

Accordingly the inventors have developed antibody colocalization microarrays to eliminate cross reactivity by spotting each dAb on the spot of the corresponding cAb on a nitrocellulose slide, see M. Pla-Roca et al in "Antibody Colocalization Microarray: A Scalable Technology for Multiplex Protein Analysis in Complex Samples" (submitted to Nature Methods). Further the inventors have also recently introduced beads-in-gel droplet microarrays which are 3D antibody microarrays made of porous alginate droplets with the entrapment of antibody-coated polystyrene microbeads that allowed for more sensitive multiplexed protein assays in serum, see for example H. Li et al. in "Hydrogel Droplet Microarrays with Trapped Antibody-Functionalized Beads for Multiplexed Protein Analysis" (Lab on a Chip, Vol. 11, pp. 528-534). Accordingly combining the processes described above in respect of FIGS. 3A and 3B in the embodiment presented in FIG. 6C results in microarray-to-microarray transfer of antibodies with the advantages of antibody colocalization microarray and of beads-in-gel droplet microarrays to produce handheld, highly sensitive and scalable multiplex immunoassay chips.

Subsequent to transfer the beads-in gel slide was evaluated using fluorescence imagery with 532 nm and 633 nm filters resulting in first optical micrograph 6000C wherein the spacing of dots on the combined slide, and hence the dAb transfer slide 6000A and assay slide 6000B was 1 mm whilst accuracy of combining the dAb transfer slide 6000A and assay slide 6000B on the prototype snap apparatus was <150 µm. It would be evident that improvements in the machining tolerances, materials, etc employed within the snap apparatus that improved tolerances may be achieved. Also shown in FIG. 6C is an optical micrograph of high density assay array 6000D comprising 16 196 spot arrays configured as 14×14 assay spots thereby providing an overall 3,136 assay locations upon a standard glass slide. Visual inspection reveals a selective and homogeneous transfer across the entire slide.

Accordingly it would be evident that by adjusting the design of the snap apparatus to accommodate larger glass slides that microarray-to-microarray transfer and assay of very high counts can be achieved with high selectivity and homogeneity.

10-Plex Sandwich Microarray-to-Microarray Immunoassays in Buffer and Serum:

To evaluate the use of microarray-to-microarray transfer for multiplexed sandwich immunoassays, we selected 10 proteins, including one breast cancer biomarker (HER 2), 4 cancer related proteins (ENG, LEP, FGF, OPN), and 5 cytokines (TNF RII, GM-CSF, CCL 2, CCL 3, IL 1β). The experiment flow employed was that shown in FIG. 3A. To avoid undesired adsorption of antibodies to the transfer chips, the spotting solution containing the detection antibody was supplemented with 1% BSA, which helped increase the transfer efficiency as BSA molecules competitively interact with surface amino groups and therefore minimize the attachment of antibodies.

Fabrication of the 10-plex sandwich immunoassays varied slightly from the process described above for other microarray assay and transfer chips as follows. After blocking with Stabilguard® for 1 h on a shaker at 320 rpm, the assay chip was incubated with the sample solutions containing the mixture of 10 proteins that were spiked into the buffer or the 10% serum solution for 1 hour on the shaker at 320 rpm. A dilution series was used to establish a binding curve with the protein concentration ranging from 200 ng/ml to 0.0128 ng/ml for the HER 2, ENG, LEP, FGF, and OPN proteins, and from 50 ng/ml to 0.0032 ng/ml for TNF RII, GM-CSF, CCL 2, CCL 3, and IL 1β proteins, with a dilution factor of 5, and a control with 0 ng/ml for all the 10 proteins.

The slide was then rinsed twice with PBST and once with PBS on the shaker at 450 rpm for 5 minutes, the slide module gasket was removed, and the slide dried under nitrogen. Next, the assay chip and the transfer chip were clamped on the snap apparatus, snapped together for 1 minute, then separated, and the assay chip was incubated in a Petri dish saturated with humidity for 1 hour. Then a slide module gasket was clamped on the assay chip, and the slide was rinsed three times with PBST and once with PBS on the shaker at 450 rpm for 5 minutes and incubated with 2.5 µg/ml of streptavidin conjugated Cy 5 for 20 minutes on the shaker at 320 rpm. The slide was then rinsed twice with PBST, once with PBS and once with DI water on the shaker at 450 rpm for 5 minutes, and dried before scanning.

Figure 7:
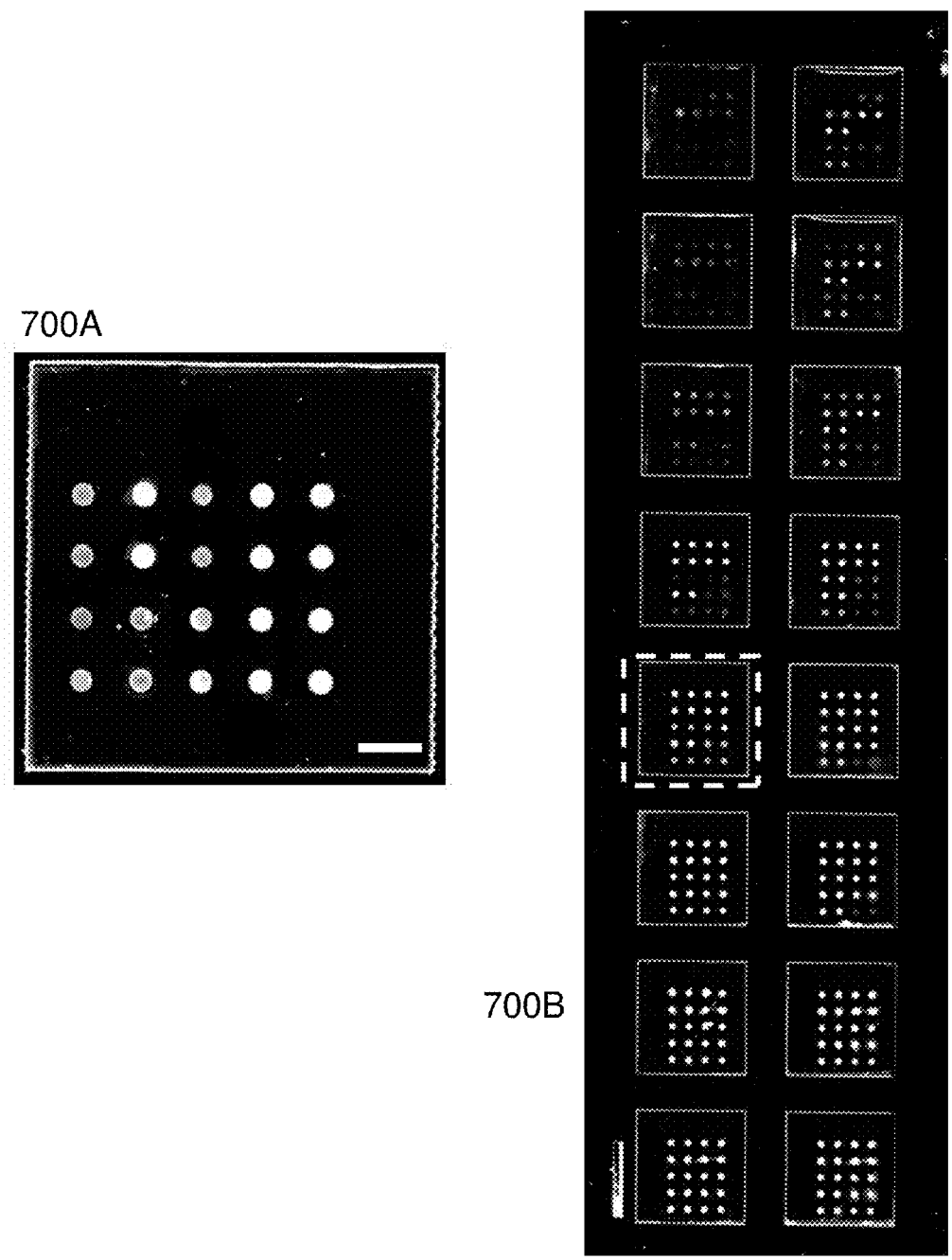
FIG. 7 depicts fluorescent micrographs of a representative slide with 16 replicate arrays incubated together with a close-up of a single array as fabricated according to an embodiment of the invention.
Figure 8:
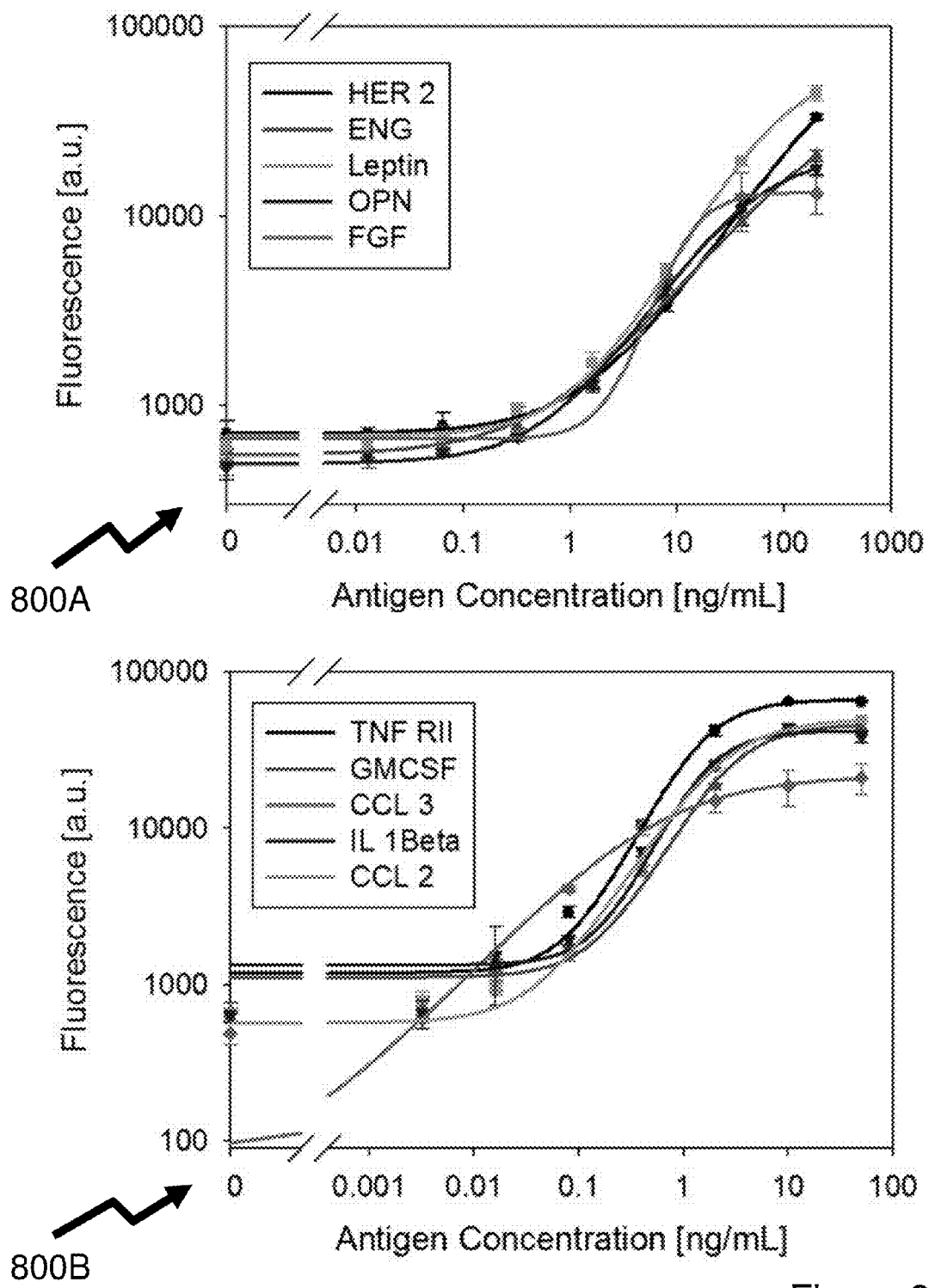
FIG. 8 depicts assay results and binding curves for antibodies in buffer solution measured using microarray-to-microarray transfer of reagents for multiplexed sandwich immunoassays according to an embodiment of the invention.

Using the microarray-to-microarray assays, the inventors obtained pg/ml sensitivity for all the 10 proteins in PBS buffer solutions, as shown in FIG. 8. Referring to FIG. 7 there is depicted a fluorescent micrograph of a representative slide 700B with 16 replicate arrays incubated with PBS and 10% serum samples, and a close-up of a single array 700A identified by the dashed lines within representative slide 700B. For scale the bar on the close-up of single array 700A is 1 mm.

From the measured fluorescent data a four-parameter logistic equation was used for curve fitting, see J. W. Findlay et al (AAPS Journal, Vol. 9, pp.E260-267) wherein 9 out of 10 curves fit the data well. FIG. 8A depicts the assay results and binding curves for HER 2, ENG, LEP, FGF, and OPN whilst FIG. 8B depicts the assay results and binding curves for TNF RII, GM-CSF, CCL 2, CCL 3, and IL 1β. As the affinity of the antibodies for these five proteins was higher that that of the other 5 proteins the assay range was adjusted. The error bars are standard deviations between triplicate experiments performed using the microarray-to-microarray snap process according to an embodiment of the invention.

The curve of CCL 3 in FIG. 8B does not fit well with the assay data at low concentrations suggesting that more optimization is needed. The LOD values of the assays are presented below in Table 1. As evident from these results for 9 out of 10 antibodies these values were lower than the LOD obtained from pin spotting colocalization immunoassays reported in the prior art, see for example see M. Pla-Roca et al in "Antibody Colocalization Microarray: A Scalable Method for Multiplexed and Quantitative Protein Profiling" (submitted to Mol. Cell. Proteomics), probably due to the better intra-spot homogeneity. Indeed, colocalization arrays are double spotted with pins, whereas for the snap chips according to embodiments of the invention both the assay chip and transfer chip are spotted with inkjet, and the antibodies on the transfer chip remain in solution. These results indicate that high sensitivity may be achieved using snap chips which might rival the one obtained with enzyme-linked immunosorbent assay (ELISA).

Figure 9:
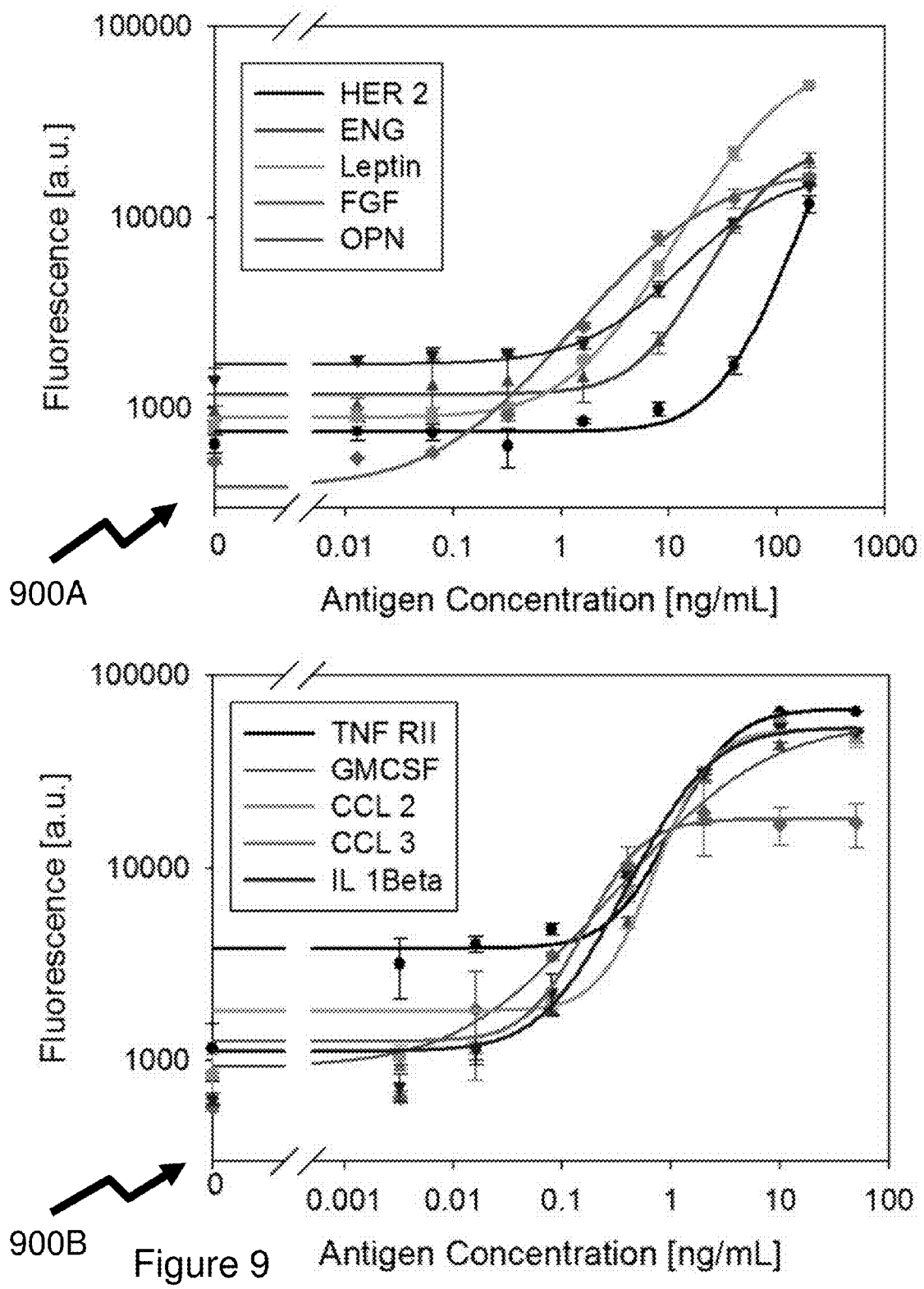
FIG. 9 depicts assay results and binding curves for antibodies in 10% serum measured using microarray-to-microarray transfer of reagents for multiplexed sandwich immunoassays according to an embodiment of the invention.

To explore the applicability of snap chips and microarray-to-microarray transfer for immunoassays using blood, the inventors performed a multiplexed assay for the same ten proteins spiked in 10% serum. These results are presented in FIG. 9 wherein FIG. 9A depicts the assay results and binding curves for HER 2, ENG, LEP, FGF, and OPN whilst FIG. 9B depicts the assay results and binding curves for TNF RII, GM-CSF, CCL 2, CCL 3, and IL 1β. The LOD of some proteins, such as TNF RII and OPN, is higher in 10% serum than in PBS which may be ascribed to interferences from matrix proteins, see for example C. Pfleger et al (J. Immunol. Methods, Vol. 329, pp. 214-218), or to endogenous patient proteins. For ENG, LEP, OPN, TNF RII, GM-CSF, CCL 2, and CCL 3, the sensitivity after correcting for the 10 fold serum dilution exceeds the physiological range for healthy persons, and for HER 2 and IL 1β it lies within the range. For example, based on the paper by Rutkowski et al. in "Cytokine Serum Levels in Soft Tissue Sarcoma Patients: Correlations with Clinico-Pathological Features and Prognosis" (Int. J. Cancer, Vol. 100, pp. 463-471), the level of TNF RII in healthy people is 3180±600 pg/ml24. The LOD for TNF RII obtained is 30 pg/ml, which is a hundred times lower than the average concentration in blood.

TABLE 1

LOD values obtained from 10-plex immunoassays in PBS and in 10% serum (pg/ml).

| Protein | LOD (3σ) | LOD (2σ) | LOD (R&D System (2σ) | Average Concentration (Healthy Control) | Reference |
|---------|----------|----------|----------------------|-----------------------------------------|-----------|
| HER 2   | 155      | 81       | n/a                  | ≤15,000                                 | Kong et al, J. Clin. Pathol., 59, 373-736 |
| ENG     | 138      | 74       | 30                   | 150,000                                 | Takahashi et al, Clin. Cancer. Res., 7, 524-532 |
| LEP     | 52       | 28       | 8                    | 26,430 ± 19,400                         | Aliustaoglu et al, Med. Oncol., 2010, 27, 388-391 |
| FGF     | 85       | 51       | 3                    | n/a                                     | n/a |
| OPN     | 263      | 171      | 24                   | 123,000                                 | Bramwell et al, Clin. Cancer. Res., 12, 3337-3343 |
| TNF RII | 36       | 21       | 2                    | 3180 ± 600                              | Rutkowski et al, Int. J. Cancer, 100, 463-471 |
| GM-CSF  | 6        | 3        | 3                    | 900 ± 90                                | Scholl et al, Breast Cancer Res. Treat., 39, 275-283 |
| CCL 2   | 15       | 10       | 5                    | 173                                     | Kim et al, Breast Cancer Res., 11, R22 |
| CCL 3   | 3        | 2        | 10                   | 88.3                                    | Kim et al, Breast Cancer Res., 11, R22 |
| IL 1β   | 14       | 8        | 1                    | 40                                      | Yurkovetsky et al, Clin. Cancer. Res., 13, 2422-2428 |

Figure 10:
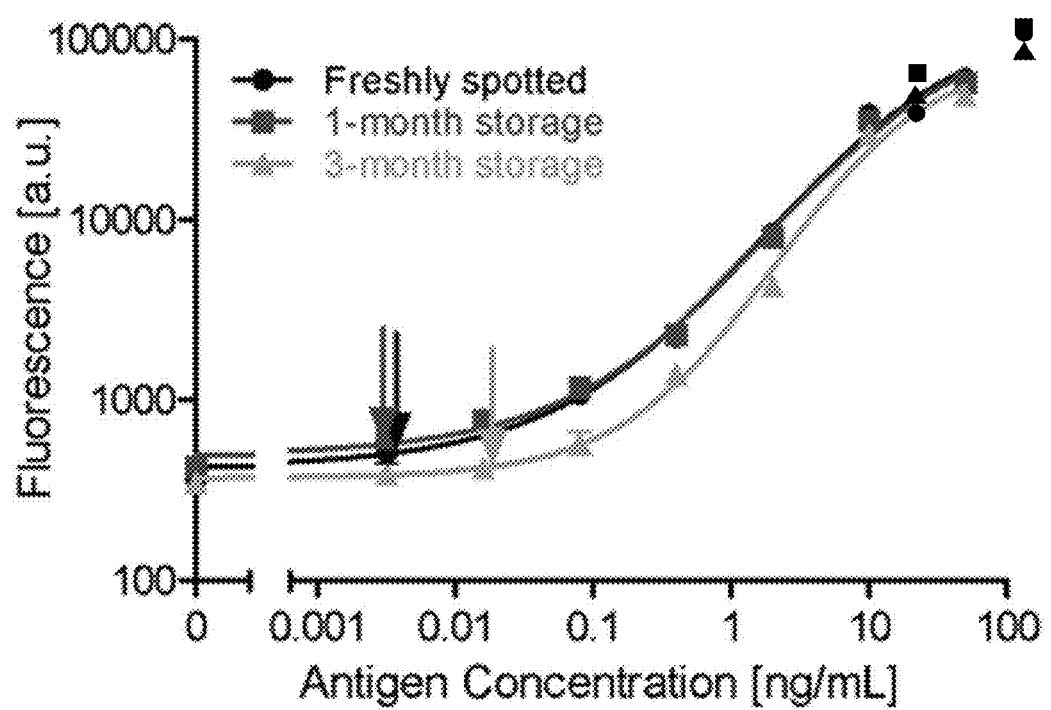
FIG. 10 depicts binding curves measured using microarray-to-microarray transfer of reagents for multiplexed sandwich immunoassays according to an embodiment of the invention as a function of storage time.

Storage of Snap Chips:

It would be evident to one skilled in the art that if the snap chip could be stored, it would allow dissociating the production of the slides which requires advanced equipment such as the inkjet spotter from the execution of the assay which can be done at low cost without need for peripheral equipment. Using TNF RII, the inventors evaluated the possibility of storing snap chips in a freezer at −20° C. wherein fluorescence measurements were made on samples after the snap fit process wherein the assay chips had been stored for 1 month and 3 months and plotted against baseline results from an as freshly spotted assay chip. Based on these results presented in FIG. 10 it appears that the antibodies loose some of their activity over time, yet the LOD obtained for 3 months storage remains well below the average physiological concentration in healthy patients for this marker. These results indicate that it is possible to store snap chips although some optimization of storage conditions rather than the simple method employed in the results presented may be necessary in order to avoid loss of activity of the antibodies, and to develop protocols for slide storage in a refrigerator at 4° C. or at room temperature as well as within freezers. Using the results presented in FIG. 10 the LOD values obtained for slides that were fresh, 1 month and 3 months old were 4 pg/ml, 3 pg/ml, and 18 pg/ml respectively. The LOD of each curve was calculated as background intensity incremented by 2σ and is indicated in FIG. 10 by the arrows for each test.

Within these experiments the inventors spotted both the assay and transfer chips, stored them for either 1 month or 3 months, and then performed the immunoassays before comparing them to freshly spotted slides. The assay chips were blocked with StabilGuard® after incubation with capture antibodies and both assay chips and transfer chips were immediately stored in an air tight bag with desiccant and placed in a −20° C. freezer. Prior to usage, the sealed bag was left at room temperature for approximately 30 minutes before opening to avoid condensation on the surface of the slides. Next, the transfer chips were incubated in a Petri dish saturated with humidity for 30 minutes to hydrate the glycerol before the antibody transfer process.

Figure 11A:
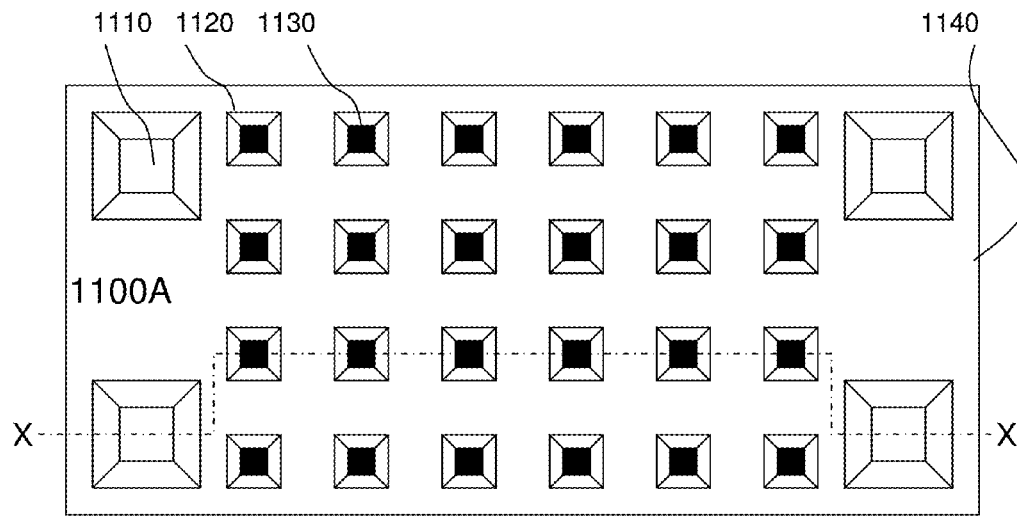
FIGS. 11A through 11C depict assay and transfer structures for microarray-to-microarray transfer of reagents for multiplexed sandwich immunoassays and resulting snap chip assembly prior to separation according to an embodiment of the invention.
Figure 11B:
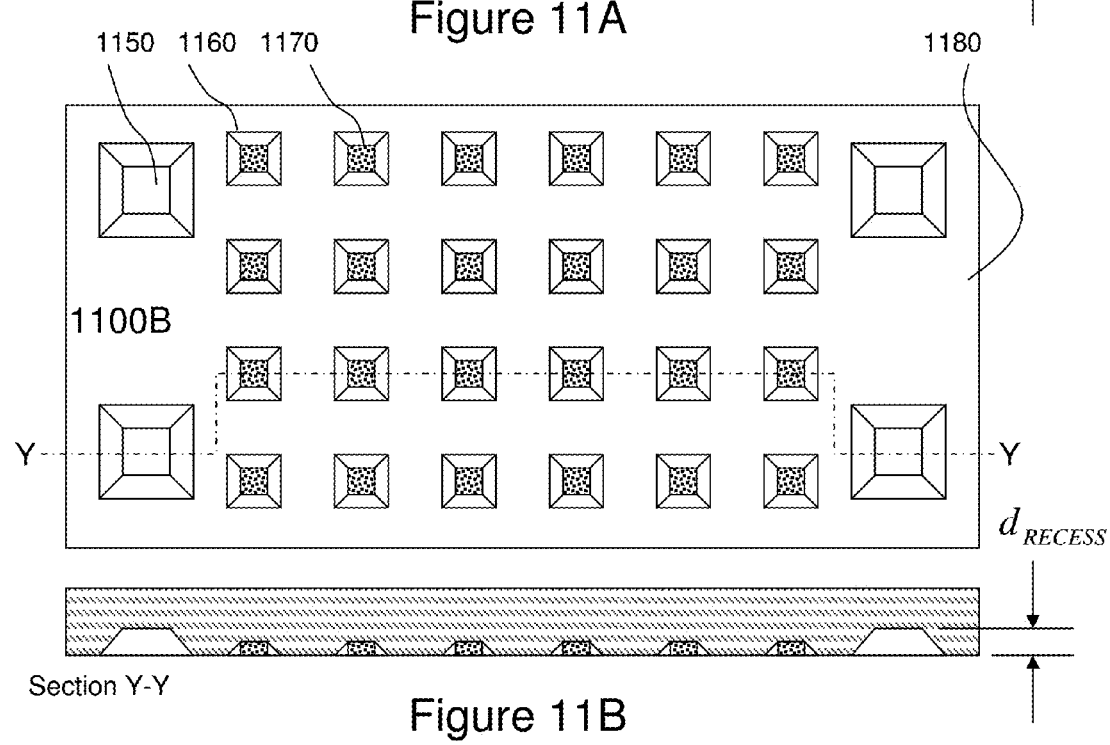
Figure 11C:
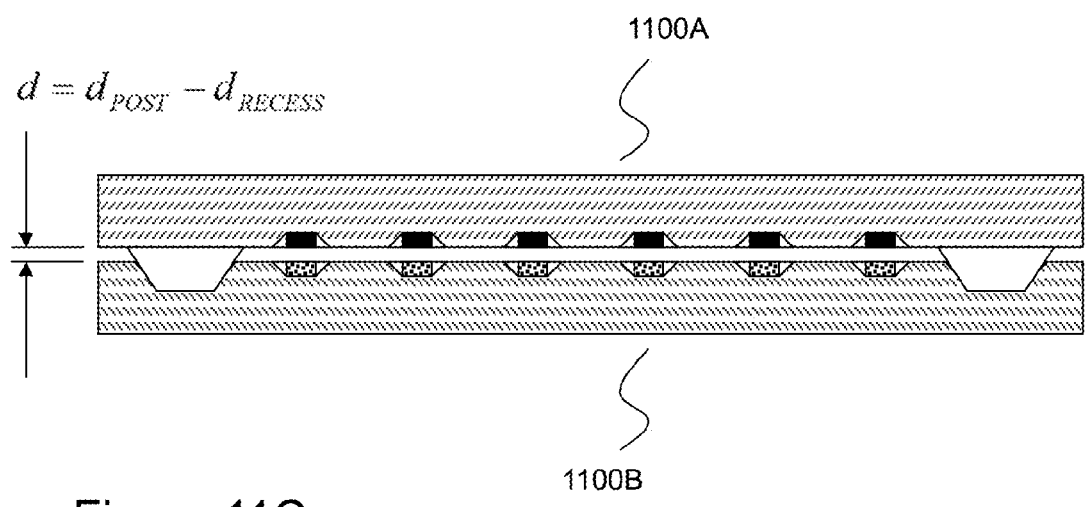

It would be evident to one skilled in the art that alternate structures may be implemented in order to provide the required snap chip assembly in order to provide microarray-to-microarray transfer of reagents for multiplexed sandwich immunoassays. Referring to FIGS. 11A through 11C there are depicted a silicon micro-machined transfer chip 1100A, silicon micro-machined assay chip 1100B, and snap chip assembly prior to separation according to an embodiment of the invention. Referring to FIG. 11A the silicon micro-machined transfer chip 1100A is depicted as comprising a silicon substrate 1140 that has been processed according to standard photolithography and semiconductor processes to provide a pattern of posts 1110 and transfer wells 1120. Patterned into the bottoms of each transfer well 1120 are aminosilane regions 1130, these being formed for example through chemical vapour deposition (CVD) or liquid phase deposition processes, see for example S. Fiorilli et al in "Vapor-Phase Self-Assembled Monolayers of Aminosilane on Plasma-Activated Silicon Substrates" (J. Colloid and Interface Science, Vol. 321, pp. 235-241) and F. Zhang et al in "Chemical Vapor Deposition of Three Aminosilanes on Silicon Dioxide: Surface Characterization, Stability, Effects of Silane Concentration, and Cyanine Dye Adsorption" (Langmuir, Vol. 26(18), pp 14648-14654). Also shown is cross-section X-X through silicon micro-machined transfer chip 1100A wherein the height of the posts 1110 of $d_{POST}$ are defined through the photolithography openings provided during processing prior to etching of the silicon.

Now referring to FIG. 11B the silicon micro-machined assay chip 1100B is depicted as comprising a silicon substrate 1180 that has been processed according to standard photolithography and semiconductor processes to provide a pattern of recesses 1150 and assay wells 1160. Patterned into the bottoms of each assay well 1160 are nitrocellulose regions 1170, these being formed for example through ultrasonic deposition, see for example C-C Chen et al in US Patent Application 2005/0,191,484 entitled "Process for Forming Nitrocellulose Films" or casting as employed by Sartorius Stedim Biotech. Also shown is cross-section X-X through silicon micro-machined assay chip 1100B wherein the depth of the recesses 1150 of $d_{RECESS}$ are defined through the photolithography openings provided during processing prior to etching of the silicon.

Now referring to FIG. 11C a cross-section of the assembled snap chip is shown comprising silicon micro-machined transfer chip 1100A and silicon micro-machined assay chip 1100B is depicted. Accordingly the post 1110 of the silicon micro-machined transfer chip 1100A has engaged the recess 1150 of the silicon micro-machined assay chip 1100B such that the two chips are aligned in the plane parallel to their surfaces and that the spacing d between the silicon micro-machined transfer chip 1100A and silicon micro-machined assay chip 1100B is accordingly defined by $d=d_{POST}-d_{RECESS}$. Accordingly the patterned aminosilane regions 1130 and nitrocellulose regions 1170 are aligned with respect to each other. Within this cross-section the droplets of detection antibodies and any formations of capture antibodies have been omitted for clarity.

It would be evident that whilst the profiles depicted for post 1110 and recess 1150 are sloped and accordingly typical of wet chemical etching of silicon as defined by its crystal planes that other techniques may be applied as are well known in the prior art for providing vertical walls to the post 1110 for example. In this case with vertical posts a coarse alignment of the silicon micro-machined transfer chip 1100A and silicon micro-machined assay chip 1100B is converted to a fine alignment as the posts 1110 move within the recesses 1150 due to the wall geometry as the silicon micro-machined transfer chip 1100A and silicon micro-machined assay chip 1100B are brought together. It would also be evident that such a micro-machined assay chip also allows for improved handling in the subsequent characterization/measurement steps.

Figure 12A:
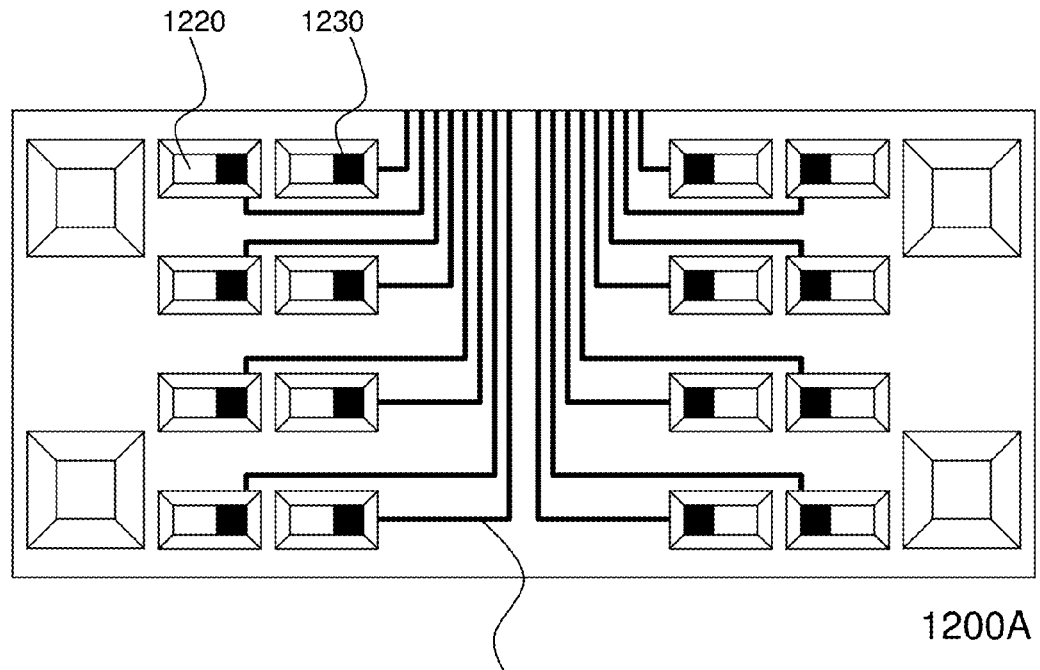
FIG. 12 depicts assay and transfer structures for microarray-to-microarray transfer of reagents for multiplexed sandwich immunoassays for a snap chip assembly featuring electrodes.
Figure 12B:
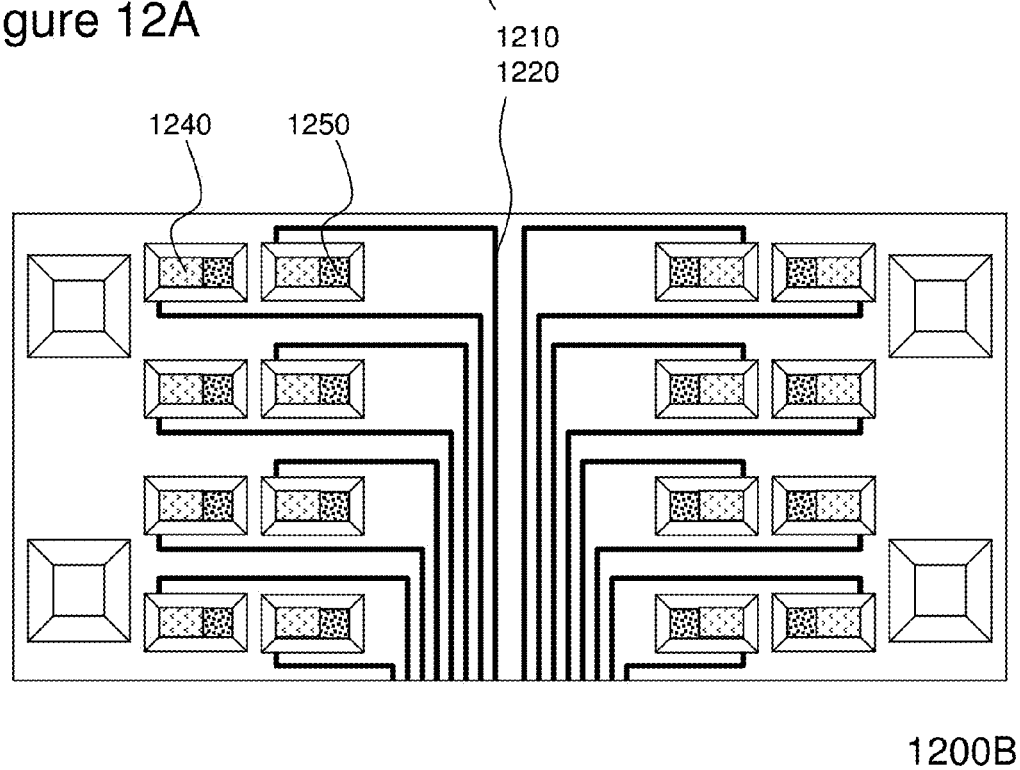

Referring to FIG. 12 there are depicted silicon micro-machined transfer chip 1200A and silicon micro-machined assay chip 1200B according to an embodiment of the invention. However, unlike silicon micro-machined transfer chip 1100A and silicon micro-machined assay chip 1100B in FIG. 11 the silicon micro-machined transfer chip 1200A and silicon micro-machined assay chip 1200B are each provided with first and second electrical contacts 1210 and 1220 respectively that couple to the transfer wells and assay wells. Within transfer wells the aminosilane regions 1230, for example, are still provided but adjacent are open regions 1220 of the transfer wells. Within the assay wells the nitrocellulose regions 1250, for example, are still provided by adjacent to these are gel regions 1240. Accordingly when assembled capture antibody and detection antibody etc are within a structure allowing application of an electric field along the length of each test cell as first electrical contact 1210 on silicon micro-machined transfer chip 1200A is at one end of the test cell and second electrical contact 1220 on the silicon machined assay chip 1200B is at the other end of the test cell.

Accordingly after assembly of the snap chip an electrical field can be applied, for example to induce electrophoresis, wherein after the electrical field is removed, the snap chip separated the silicon micro-machined assay chip 1200B can be tested but now due to the well defined structural characteristics of the silicon micro-machined assay chip 1200B the fluorescent probe, or whatever characterization technique is employed, can be located accurately one or other end of the test cells according to the particular testing being performed. It would be evident that such a technique may also be modified to include the option to provide the capture antibodies at the opposite end of each test cell so that electrophoresis etc is performed such that the transported protein is then captured. Optionally first and second electrical contacts 1210 and 1220 could be provided on one of the silicon micro-machined assay chip 1200B and silicon micro-machined transfer chip 1200A.

Figure 13:
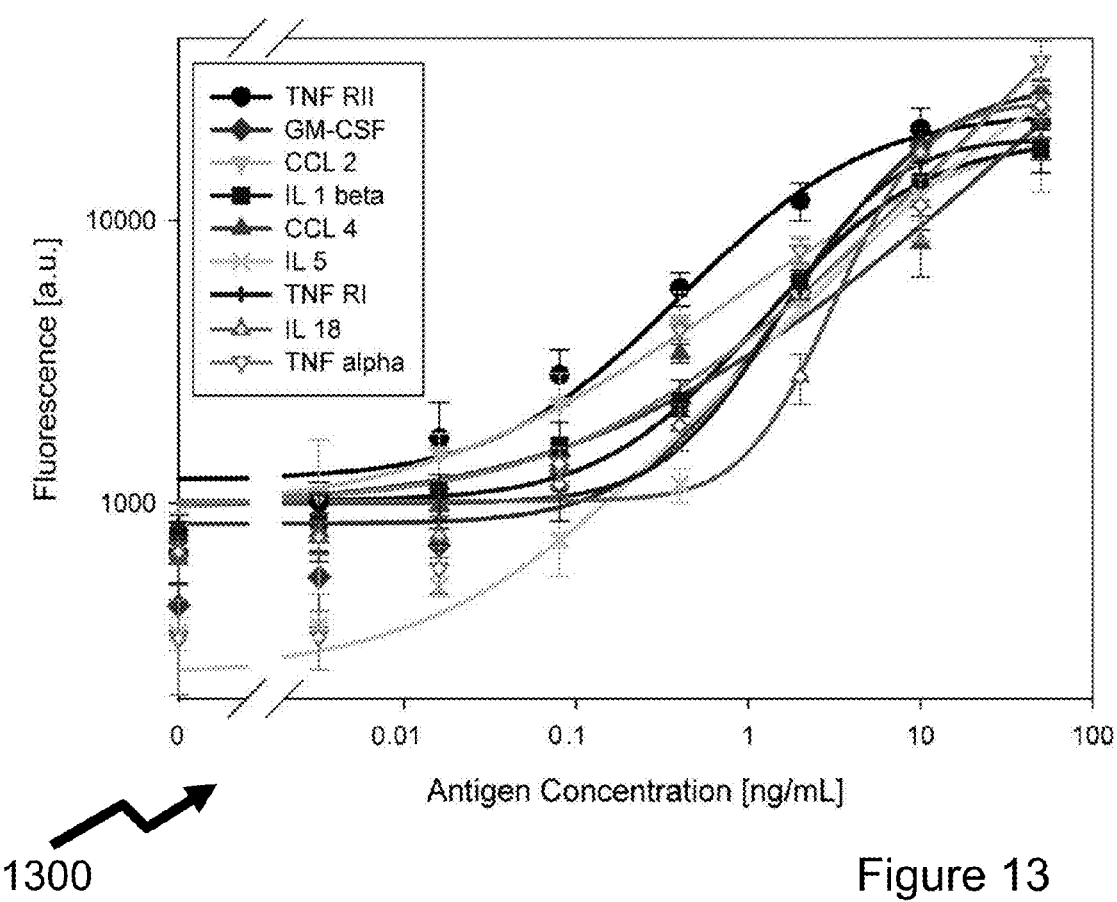
FIG. 13 depicts assay results and binding curves for 9 different Ab pairs measured using microarray-to-microarray transfer of reagents according to an embodiment of the invention.

Referring to FIG. 13 the applicability of snap chips and microarray-to-microarray transfer for immunoassays exploiting antibody colocalization microarray and beads-in-gel droplet microarrays as discussed above was demonstrated with 9 different antibody pairs. These results presented in graph 1300 depict the assay results and binding curves for TNF RII, GM-CSF, CCL 2, IL 1 Beta, CCL 4, IL 5, TNF RI, IL 18 and TNF Alpha. The limit of detection achieved in this experiment being in the pg/ml range for all analytes, and specifically 3 pg/ml for TNF RII (Tumor Necrosis Factor Receptor-II).

Double Snap:

Within embodiments of the invention described above in respect of microarray-to-microarray transfer of immunoassays and their exploitation in multiplexed sandwich arrays a factor severely limiting the performance of these multiplexed sandwich assays is cross reactivity. However, this may be overcome by exploiting antibody colocalization microarrays (ACMs), see for example Pla-Roca et al in "Antibody Colocalization Microarray: A Scalable Technology for Multiplex Protein Analysis in Complex Samples" (Molecular & Cellular Proteomics, Vol. 11, pp. 1-12). ACM requires spotting with capture antibodies (cAbs) and detection antibodies (dAbs) to the same spot during the assay, which is challenging. To simplify the ACM the microarray-to-microarray transfer method described above in respect of FIGS. 3A through 13 was developed by the inventors to deliver antibodies from an array of droplets to an array of spots by snapping two slides, an assay slide and transfer slide, together. However, the mirror setup configuration of this approach can create alignment issues due to the imprecision of inkjet spotters. As described supra 10 proteins were measured simultaneously with this microarray-to-microarray transfer of immunoassays, commonly referred to by the inventors as snap chip, but extension to ACM and increased simultaneous protein counts is limited by this inkjet spotter imprecision. Accordingly, the inventors have established Double Snap Chip (DSC) which overcomes the alignment issues and enables higher density, and very high sensitivity multiplex immunoassays.

Figure 14:
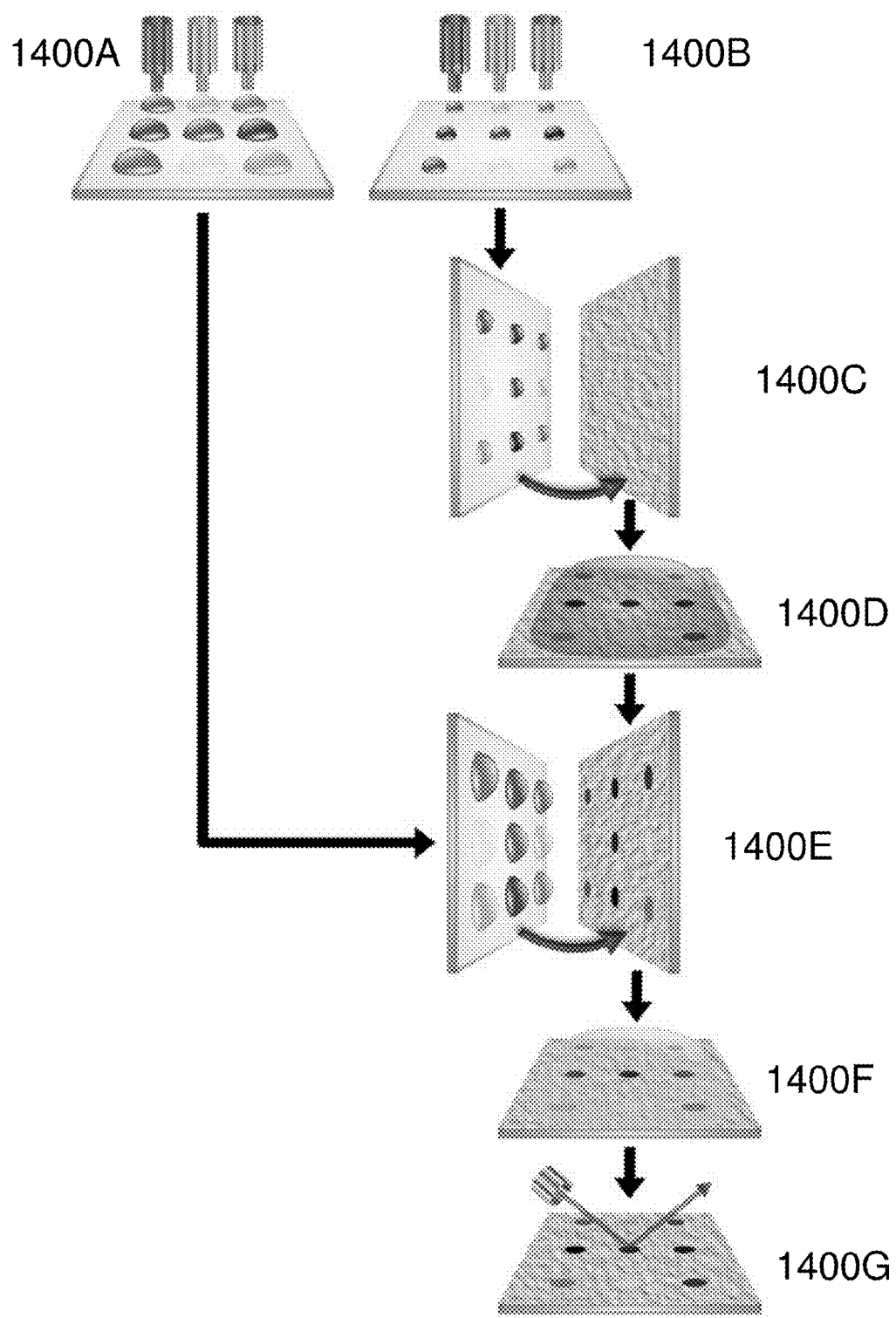
FIG. 14 depicts a process flow for double snap-chip based microarray-to-microarray transfer of reagents for multiplexed sandwich immunoassays according to an embodiment of the invention.

Referring to FIG. 14 there is depicted a process flow for double snap-chip based microarray-to-microarray transfer of reagents for multiplexed sandwich immunoassays according to an embodiment of the invention. Initially cAbs and dAbs are spotted with an inkjet spotter onto aminosilane slide in steps 1400B and 1400A respectively. The dAbs slide in the experiments reported below in respect of FIGS. 16, 17A, and 17B were performed wherein the dAbs slide was stored at −20° C. after spotting. However, it would be apparent that other protocols may be employed. The cAbs were transferred onto a nitrocellulose slide by snapping for 1 minute as indicated by process step 1400C. The resulting assay slide was blocked, dried, and stored. For assays, slides were removed from the freezer, and the nitrocellulose slide incubated with a sample overnight, and dried as indicated by process step 1400D. Next, the processed nitrocellulose slide and dAb slide were snapped together as indicated in step 1400E and then incubated for 1 hour. Upon rinsing and subsequent incubation with streptavidin-Cy 5 as indicated in process step 1400F the assay results are obtained using a scanner as indicated in process step 1400G.

Figure 15:
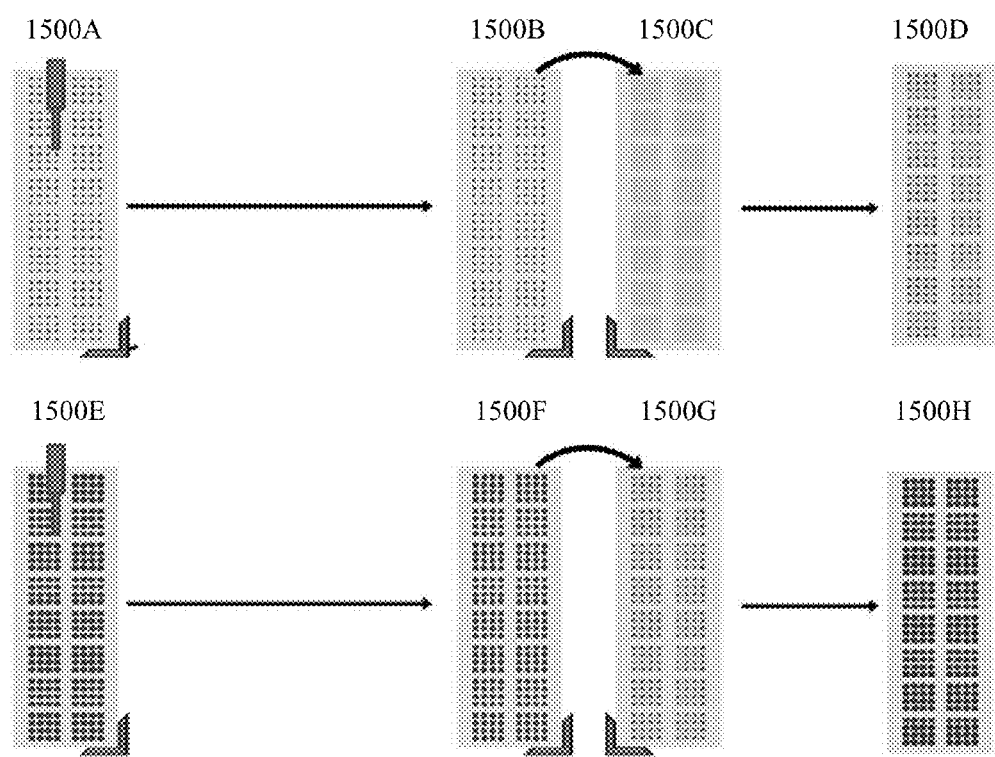
FIG. 15 depicts a detailed schematic of the double snap-chip based microarray-to-microarray transfer of reagents for multiplexed sandwich immunoassays according to an embodiment of the invention presented in FIG. 14.

Referring to FIG. 15 there is depicted a detailed schematic of the double snap-chip based microarray-to-microarray transfer of reagents for multiplexed sandwich immunoassays according to an embodiment of the invention presented in FIG. 14. As depicted cAbs are spotted on a cAb slide (1500A) which was mechanically aligned to the bottom-right corner of an alignment system (1500B) such as described above in respect of FIGS. 5A through 5D. Next a cAb slide and an assay slide (1500C) are pushed to bottom right and bottom left corner of the snap apparatus chucks and snapped together resulting in first slide 1500D wherein upon separation the cAb has been transferred to the assay slide. Next the same sequence of printing (1500E), insertion into snap apparatus chuck (1500F), insertion of assay slide into snap apparatus chuck (1500G) and transfer of the dAb to the assay slide upon separation (1500H) is performed. Thus both the spotting and transfer of the cAb and dAb arrays are each done in the same reference frames of the inkjet spotter and snap apparatus the issues of angular misalignment occurring because the inkjet spotter and slides are not perfectly orthogonal or potential non-straight shooting by the inkjet spotter are reduced significantly.

Figure 16:
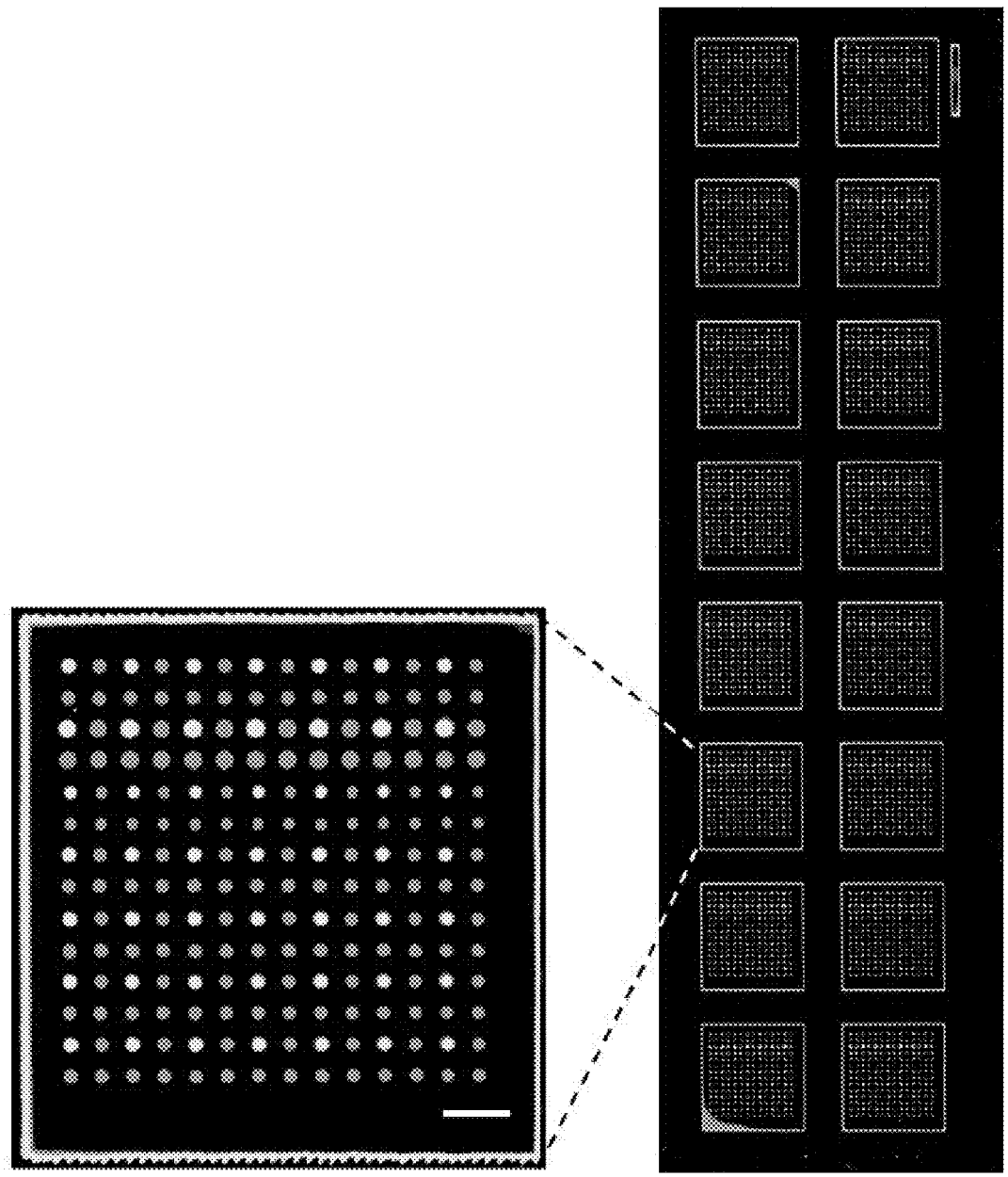
FIG. 16 depicts a scan of an assay slide with 3,136 spots using the double snap chip process described above in respect of FIG. 14.
Figure 17A:
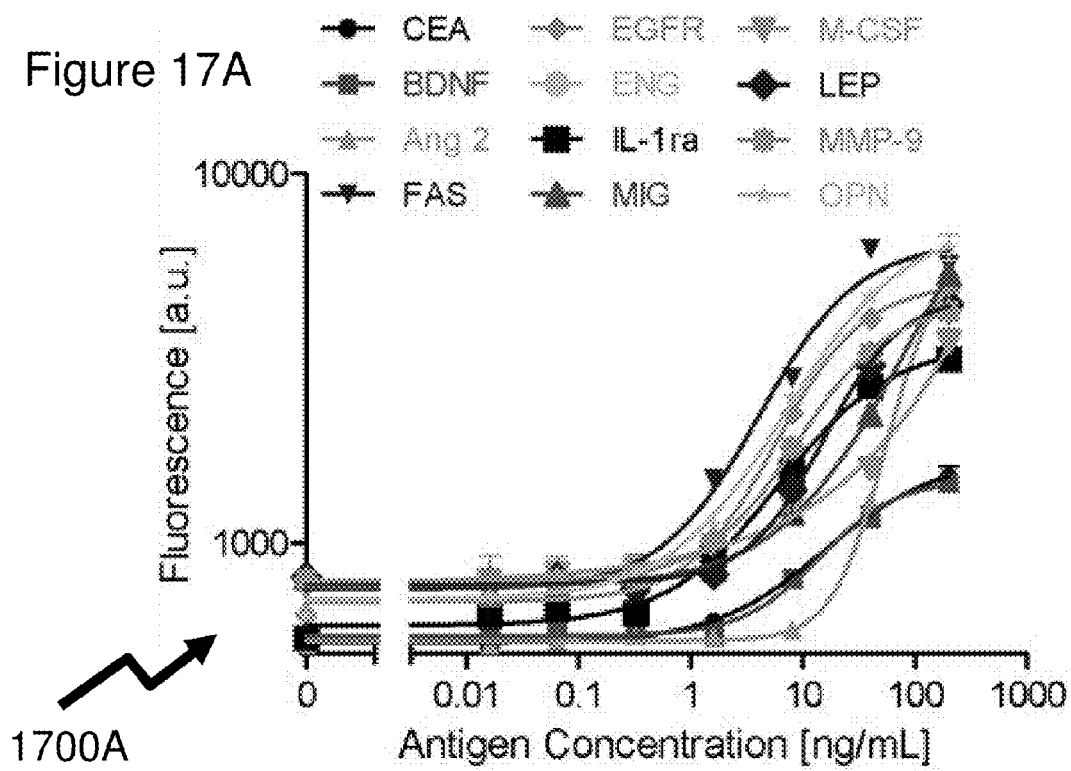
FIGS. 17A and 17B depict binding curves for 40 proteins measured simultaneously measured using microarray-to-microarray transfer of reagents according to an embodiment of the invention.
Figure 17A:
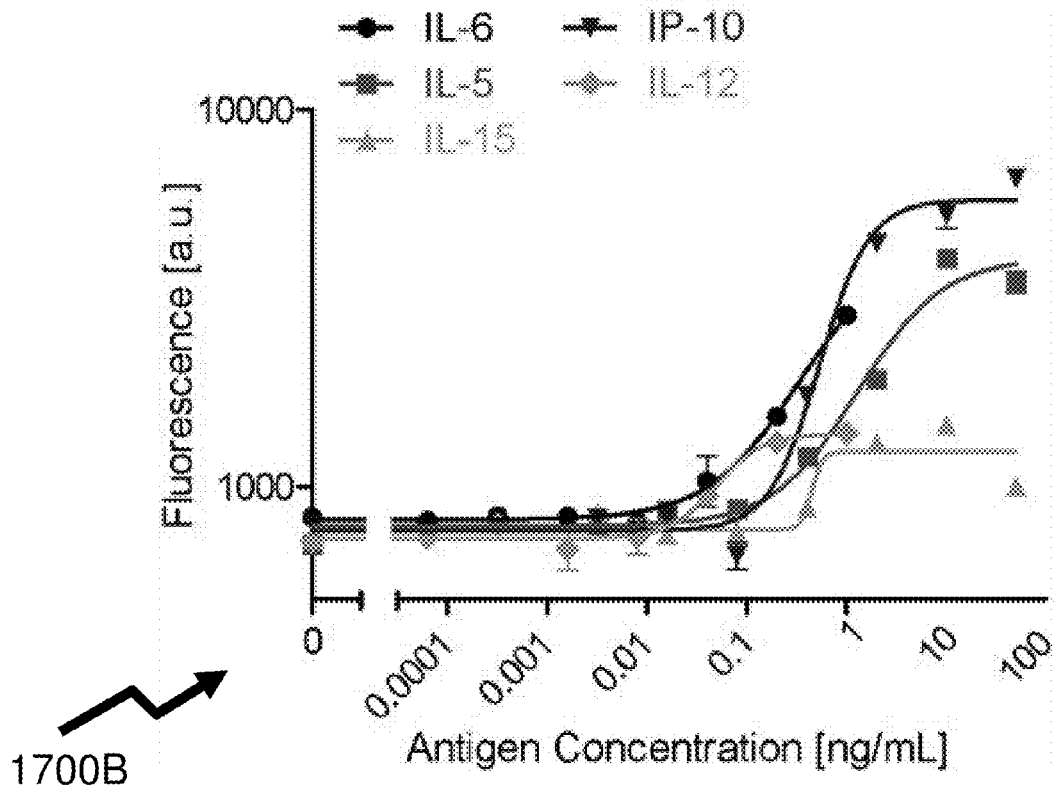
Figure 17B:
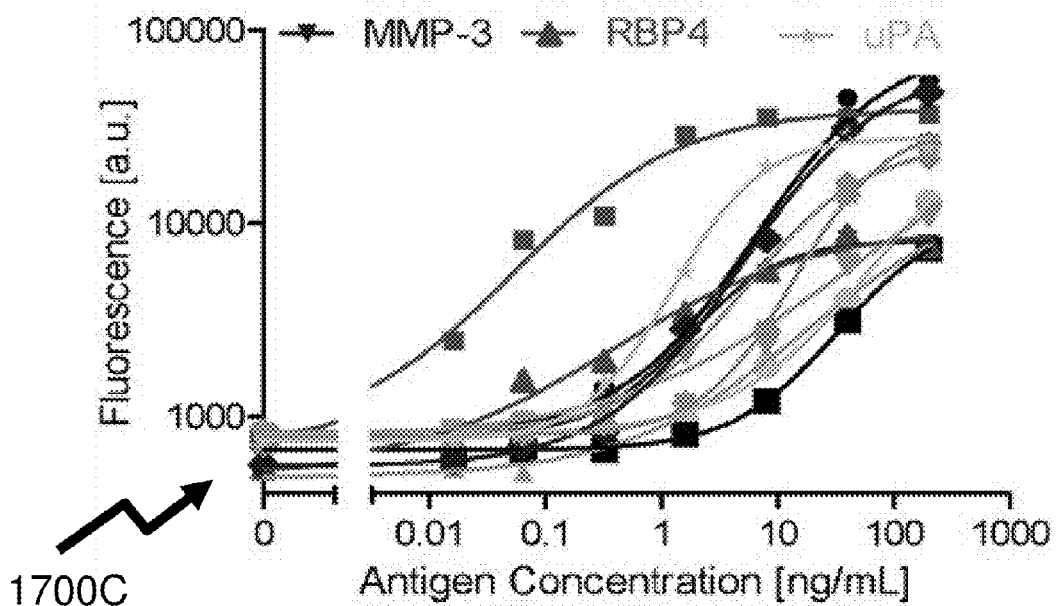
Figure 17B:
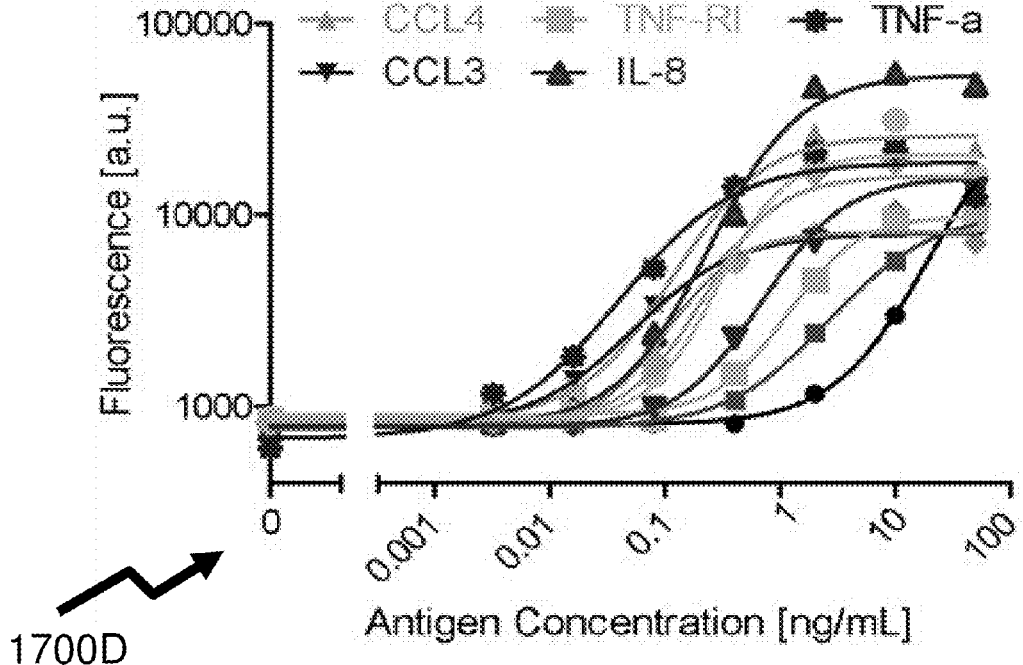

In the snap chip results presented supra the array density was approximately 130 spots/cm$^2$ due to the mirroring induced misalignments. With the DSC methodology of sequentially transferring the cAb array and upon sample incubation the dAb array onto a slide, as depicted in FIGS. 14 and 15 the average center-to-center distance between aligned spots was reduced to 30 μm although other spacing were also employed, the largest being 80 μm. Accordingly the array density is increased to 400 spots/cm$^2$. Accordingly as depicted in FIG. 16 3136 spots were completed with zero failures using an alignment apparatus such as described in respect of FIG. 5A. FIG. 16 depicts a scan of an assay slide after transfer using 532 nm and 633 nm laser sources. Alexa 532 labeled goat IgG functioned as cAbs, and Alexa 633 labeled anti-goat IgG were spotted and transferred on every second spot. The center-to-center spacing between the spots in this instance was 450 μm. The variations in spot size between rows are presumed to be due to inkjet spotting which was done two rows at a time. The scale bar is 1 mm.

Using the DSC technique immunoassays were performed for 40 proteins simultaneously. The results from this are presented in first to fourth graphs 1700A to 1700D in FIGS. 17A and 17B. The results are split based upon fluorescent intensity and antigen concentrations for readability rather than antigen type. For 36 of the proteins the measured LODs were in the pg/ml range with the best being EGF which was measured at 1.1 pg/ml DSC as with the single snap chip approach allows high sensitivity, multiplexed immunoassays to be performed with low handling complexity and reduced process complexity. Assay slides with cAbs and dAbs can be prepared ahead of time and stored, thus avoiding the need of a microarrayer during the assay process. This for end users of such techniques is of great practical importance as it allows immunoassays to be performed in a wider range of environments rather than solely well equipment clinical analysis laboratories. As presented above the DSC could be extended to 1,568 targets assuming duplicate spots, and to further higher counts with improved spotting. The DSC approach therefore provides a useful and powerful tool for antibody-based proteomics, notably for biomarker discovery and validation in blood for cancer and other diseases It would be evident to one skilled in the art that whereas glass and silicon have been presented for providing the transfer chip and assay chip that combinations thereof may also be employed as well as other materials including but not limited ceramics, plastics, and glasses not usually associated with glass slides as the provide enhanced characteristics such as for example being molded with enhanced dimensional control. It would be evident that in other embodiments of the invention that the manufacturing tolerances of the clam shell as discussed supra in respect of FIG. 5C may be sufficient that similarly toleranced substrates for the assay chip 5200 and transfer chip 5300 may be inserted and interfaced without the requirement for the rubber elements 5500.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A microarray-to-microarray transfer assembly comprising:
   an assay chip comprising a plurality of first locations disposed on a surface of the assay chip to form a first array, each first location defined by first coordinates relative to a predetermined point on the assay chip;
   a transfer chip comprising a plurality of second locations disposed on a surface of the transfer chip to form a second array, each second location defined by second coordinates relative to a predetermined point on the transfer chip having a predetermined relationship with the predetermined point on the assay chip, the first array and the second array being mirror patterns of each other; and
   a snap apparatus comprising:
      a first element defining a first recess sized for receiving, aligning, and retaining the assay chip therein;
      a second element defining a second recess sized for receiving, aligning and retaining the transfer chip therein; and
      at least one spacer between the assay chip and the transfer chip, sized to separate the assay chip and the transfer chip by a predetermined distance when the first element and the second element are brought together while allowing a liquid bridge to form between a first material on the assay chip and a second material on the transfer chip.

2. The assembly of claim 1, wherein the snap apparatus further comprises at least one clamp to apply a pressure to the first element and the second when they are brought together.

3. The assembly of claim 1, wherein the first element and the second element are made from optically transparent materials.

4. The assembly of claim 1, wherein one of the first element and the second element comprises at least one rod and the other of the first element and the second element comprises at least one rod receiving hole, for engaging the first element and the second element together.

5. The assembly of claim 1, wherein the first element and the second element each comprise a rubber element positioned within the recess to retain a respective one of the assay chip and the transfer chip.

6. The assembly of claim 1, wherein the first element and the second element are joined by at least one first hinge.

7. The assembly of claim 6, wherein one of the first element and the second element comprises at least one pillar and the other of the first element and the second element comprises at least one pillar receiving hole, for engaging the first element and the second element together.

8. The assembly of claim 1, wherein the first element and the second element are formed from injection-molding material.

9. The assembly of claim 6, further comprising a third element defining a third recess sized for receiving, aligning and retaining an additional chip therein, the third element attached to the first element by at least one second hinge.

10. A method for microarray-to-microarray transfer, the method comprising:
 inserting an assay chip into a first recess of a first element of a snap apparatus, the assay chip comprising a plurality of first locations disposed on a surface of the assay chip to form a first array, each first location defined by first coordinates relative to a predetermined point on the assay chip, the first recess sized for receiving, aligning, and retaining the assay chip therein, at least one of the first locations comprising a first material;
 inserting a transfer chip into a second recess of a second element of the snap apparatus, the transfer chip comprising a plurality of second locations disposed on a surface of the transfer chip to form a second array, each second location defined by second coordinates relative to a predetermined point on the transfer chip having a predetermined relationship with the predetermined point on the assay chip, the first array and the second array being mirror patterns of each other, the second recess sized for receiving, aligning and retaining the transfer chip therein, at least one of the second locations corresponding to the at least one of the first locations comprising a second material;
 providing a spacer between the assay chip and the transfer chip, the spacer sized to separate the assay chip and the transfer chip by a predetermined distance when the first element and the second element are brought together; and
 closing the snap apparatus by bringing the first element and the second element together to form a liquid bridge between the first material and the second material.

11. The method of claim 10, wherein closing the snap apparatus comprises clamping the first element and the second element together to apply pressure thereto.

12. The method of claim 10, wherein closing the snap apparatus comprises inserting at least one rod extending from one of the first element and the second element into at least one hole provided on the other of the first element and the second element.

13. The method of claim 10, wherein closing the snap apparatus comprises rotating the first element and the second element about a hinge connecting the first element and the second element together.

14. The method of claim 13, wherein closing the snap apparatus comprises inserting at least one pillar extending from at least one of the first apparatus and the second apparatus into at least one hole provided on the other of the first element and the second element.

15. The method of claim 10, further comprising:
 separating the first element and the second element;
 inserting an additional chip into a third recess of a third element, the third recess sized for receiving, aligning, and retaining the additional chip therein; and
 bringing together the first element and the third element.

* * * * *